United States Patent [19]
Linsley et al.

[11] Patent Number: 5,770,197
[45] Date of Patent: *Jun. 23, 1998

[54] METHODS FOR REGULATING THE IMMUNE RESPONSE USING B7 BINDING MOLECULES AND IL4-BINDING MOLECULES

[75] Inventors: Peter S. Linsley; Jeffrey A. Ledbetter, both of Seattle; Nitin K. Damle, Renton; William Brady, Bothell; Philip M. Wallace, Seattle, all of Wash.

[73] Assignee: Bristol-Myers Squibb Company, Princeton, N.J.

[*] Notice: The term of this patent shall not extend beyond the expiration date of Pat. No. 5,434,131.

[21] Appl. No.: 8,898

[22] Filed: Jan. 22, 1993

Related U.S. Application Data

[63] Continuation-in-part of Ser. No. 723,617, Jul. 27, 1991, abandoned.

[51] Int. Cl.$^6$ ...................... A61K 39/395; C07K 14/705; C07K 16/46
[52] U.S. Cl. .................................... 424/134.1; 424/139.1; 424/144.1; 424/192.1; 424/810; 530/350; 530/388.7; 530/868; 435/69.7
[58] Field of Search .......................... 435/69.7; 530/386, 530/378.1, 387.3, 350, 388.7, 868; 536/23.5; 935/10; 514/2; 424/85.8, 134.1, 139.1, 144.1, 192.1, 810

[56] References Cited

U.S. PATENT DOCUMENTS

| | | | |
|---|---|---|---|
| 4,399,216 | 8/1983 | Axel et al. | 435/6 |
| 4,683,195 | 7/1987 | Mullis et al. | 435/6 |
| 4,683,202 | 7/1987 | Mullis | 435/91 |
| 5,434,131 | 7/1995 | Linsley et al. | 514/2 |

FOREIGN PATENT DOCUMENTS

| | | |
|---|---|---|
| WO 92/15671 | 9/1992 | WIPO. |
| WO 93/00431 | 1/1993 | WIPO. |

OTHER PUBLICATIONS

Schwartz, Constimulation of T Lymphocytes: The Role of CD28, CTLA–4, and B7/BB1 in Interleukin–2 Production and Immunotherapy, Cell 71, pp. 1065–1068. 1992.
Tan et al., Induction of Alloantigen–specific Hyporesponsiveness in Human T Lymphocytes by Blocking Interaction of CD28 with Its Natural Ligand B7/BB1, J. Exp. Med, 177, pp. 165–173, 1993.
Sechzer, The Role of Animals in Biomedical Research "The Use of Short Term in Vitro adn Submammalian Tests as Alternatives to Large Scale Animal Bioassays" (1993) The New Academy of Sciences, at pp.68–73.
Long–Term Animal Studies, Their Predictive Value for Man, Edited by Stuart R. Walker and Anthony D. Dayan, 1986, Chapter 1,3, pp. 17–22.
Janeway, "Approaching the Asymptote? Evolution and Revolution in Immunology", *Cold Spring Harbor Symp. Quant. Biol.*LIV:1–13 (1989).
Shaw and Shimuzu, "Two Molecular Pathways of Human T Cell Adhesion ; Establishment of Receptor–Ligand Relationship", *Current Opinion in Immunology*. Eds. Kindt and Long, 1:92–97 (1988).
Hemler, "Adhesive Protein Receptors on Hematopoietic Cells", *Immunology Today*9:109–113 (1988).
Kakiuchi et al., "B Cells as Antigen–Presenting Cells : The Requirement for B Cell Activation", *J. Immunol.* 131:109–114 (1983).
Krieger et al., "Antigen Presentation by Splenic B Cells: Resting B Cells are Ineffective, Whereas Activated B Cells are Effective Accessory Cells for T Cells Responses", *J. Immunol.* 135:2937–2945 (1985).
McKenzie, "Alloantigen Presentation by B Cells—Requirement for IL–1 and IL–6". *J. Immunol.* 141:2907–2911 (1988).
Hawrylowicz and Unanue, "Regulation of Antigen–Presentation–I IFN–$\gamma$ Induces Antigen–Presenting Properties on B Cells", *J. Immunol.* 141:4083–4088 (1988).
Springer et al., "The Lymphocyte Function–Associated LFA–1, CD2, and LFA–3 Molecules: Cell Adhesion Receptors of the Immune System", *A. Rev. Immunol.* 5:223–252 (1987).
Dinarello and Mier, "Current Concepts –Lymphokines", *New Engl. Jour. Med.* 317:940–945 (1987).
Weiss et al., "The Role of the T3/Antigen Receptor Complex in T–Cell Activation", *Ann. Rev. Immunol.* 4:593–619 (1986).
McMichael, Ed., "Non–Lineage, LFA–1 Family, and Leucocyte Common Antigens: New and Previously Defined Clusters", *Leukocyte Typing III,*Oxford Univ. Press, Oxford, UK (1987).
Moingeon et al., "CD2–mediated Adhesion Facilitates T Lymphocyte Antigen Recognition Function", *Nature*339:312–314 (1988).
Makgoba et al., ICAM–1 A Ligand for LFA–1–Dependent Adhesion of B, T and Myeloid Cells. *Nature*331:86–88 (1988).
Stauntion et al., "Functional Clonging of ICAM–2 A Cell Adhesion Ligand for LFA–1 Homologous t ICAM–1", *Nature*339:61–64 (1989).
Norment et al., "Cell–Cell Adhesion Mediated by CD8 and MHC Class I Molecules", *Nature*336:79–81 (1988).
Doyle and Strominger, "Interaction Between CD4 and Class II MHC Molecules Mediates Cell Adhesion", *Nature*330:256–259 (1987).
Stoolman, "Adhesion Molecules Controlling Lymphocyte Migration", *Cell*56:907–910 (1989).

(List continued on next page.)

*Primary Examiner*—Lorraine M. Spector
*Attorney, Agent, or Firm*—Merchant, Gould, Smith, Edell, Welter & Schmidt

[57] ABSTRACT

The invention identifies the CTLA4 receptor as a ligand for the B7 antigen. The complete amino acid sequence encoding human CTLA4 receptor gene is provided. Methods are provided for expressing CTLA4 as an immunoglobulin fusion protein, for preparing hybrid CTLA4 fusion proteins, and for using the soluble fusion proteins, fragments and derivatives thereof, including monoclonal antibodies reactive with B7 and CTLA4, to regulate T cell interactions and immune responses mediated by such interactions.

11 Claims, 15 Drawing Sheets

OTHER PUBLICATIONS

Brescher and Cohn, "A Theory of Self–Nonself Discrimination", *Science* 169:1042–1049 (1970).

Freeman et al., "B7 A New Member of the Ig Superfamily with Unique Expression on Activated and Neoplastic B Cells", *J. Immunol.* 143(8):2714–2722 (1989).

Freedman et al., "B7 A B Cell–Restricted Antigen that Identifies Preactivated B Cells", *J. Immunol.* 138:3260–3267 (1987).

Clark et al., "Polypeptides on Human B Lymphocytes Associated with Cell Activation", *Human Immunol.* 16:100–113 (1986).

Yokochi et al., "B Lymphoblast Antigen (BB–1) Expressed on Epstein–Barr Virus–Activated B Cells Blasts, B Lymphoblastoid Cell Lines, and Burkitt's Lymphomas", *J. Immunol.* 128:823–827 (1981).

Weiss, "Structure and Function of the T Cell Antigen Receptor", *J. Clin, Invest.* 86:1015–1022 (1990).

Allen, "Antigen Processing at the Molecular Level", *Immunol. Today* 8:270–273 (1987).

Schwartz, "A Cell Culture Model for T Lymphocytes Clonal Anergy", *Science* 248:1349–1356 (1990).

Weaver and Unanue, "The Costimulatory Function of Antigen–Presenting Cells", *Immunol. Today* 11:49–55.

Aruffo and Seed, "Molecular Cloning of a CD28 cDNA by a High–Efficiency COS Cell Expression System", *Proc. Natl. Acad. Sci.* 84:8573–8577 (1987).

Damle et al., "Alloantigen–Sepcific Cytotoxic and Suppressor T Lymphocytes are Derived from Phenotypically Distinct Precursors", *J. Immunol.* 131:2296–2300 (1983).

June et al., "T–Cell Proliferation Involving the CD28 Pathway is Associated with Cyclosporine–Resistant Interleukin 2 Gene Expression", *Mol. Cell. Biol.* 7:4472–4481 (1987).

Thompson et al., "CD28 Activation Pathway Regulates the Production of Multiple T–Cell–Derived Lymphokines/Cytokines", *Proc. Natl. Acad. Sci.* 86:1333–1337 (1989).

Lindsten et al. "Regulation of Lymphokine Messenger RNA Stability by a Surface–Mediated T Cell Activation Pathway", *Science* 244:339–343 (1989).

Damle et al., "Monoclonal Antibody Analysis of Human T Lymphocyte Subpopulations Exhibiting Antologous Mixed Lymphocyte Reaction", *Proc. Natl. Acad. Sci.* 78:5096–5098 (1981).

Lesslauer et al., "T90/44 (9.3 Antigen). A Cell Surface Molecule with a Function in Human T Cell Activation", *Eur. J. Immunol.* 16:1289–1296 (1986).

Linsley et al., "T–Cell Antigen CD28 Mediates Adhesion with B Cells by Interacting with Activation Antigen B7/BB–1", *Proc. Natl. Acad. Sci. USA,* 87:5031–5035 (1990).

Linsley et al., "Binding of the B Cell Activation Antigen B7 to CD28 Costimulates T Cell Proliferation and Interleukin 2 mRNA Accumulation ", *J. Exp. Med.* 173:721–730 (1991).

Kohno et al., CD28 Molecule as a Receptor–Like Function for Accessory Signals in Cell–Mediated Augmentation of IL–2 Production, *Cell Immunol.* 131:1–10 (1990).

Brunet et al., "A New Member of the Immunoglobulin Superfamiluy –CTLA–4", *Nature* 328:267–270 (1987).

Brunet et al., "A Differential Molecular Biology Search for Genes Preferentially Expressed in Function T Lymphocytes: The CTLA Genes", *Immunol. Rev.* 103:21–36 (1988).

Dariavach et al., "Human Ig Superfamily CTLA–4 Gene: Chromosomal Localization and Identity of Protein Sequence Between Murine and Human CTLA–4 Cytoplasmic Domains, " *Eur. J. Immunol.* 18:1901–1905 (1988).

Lafage–Pochitaloff et al., "Human CD28 and CTLA–4 Ig Superfamily Genes are Located on Chromosome 2 at Bands q33–q34", *Immunogenetics* 31:198–201 (1990).

Capon et al., "Designing CD4 Immunoadhesins for AIDS Therapy", *Nature* 337:525–531 (1989).

Mullis & Faloona, *Methods Enzymol.* 154:335–350 (1987).

Fiers, et al., *Nature* 273:113 (1987) (Exhibit 46).

Karin, et al., *Nature* 299:797–802 (1982).

Toyama and Okayama, *FEBS* 268:217–221 (1990).

Hitzeman et al., *J. Biol. Chem.* 255:12073 (1980).

Goeddel et al., *Nucleic Acids Res.* 8:4057 (1980).

Shimatake et al., *Nature* 292:128 (1981).

Sanger et al., *Proc. Natl. Acad. Sci. USA* 74:5463 (1977).

Messing et al., *Nucleic Acids Res.* 9:309 (1981)..

Maxam et al., *Methods Enzymol.* 65:499 (1980).

Kohler and Milstein ( see Kohler and Milstein, *Nature,* 256:495–497 (1975).

Zola et al., in *Monoclonal Hybridoma Antibodies: Techniques and Applications,* Hurell (ed.) pp. 51–52 ( CRC Press, 1982).

Fink et al., *Prog. Clin. Pathol.,* 9:121–133 (1984), Fig. 6–1 at p. 123).

Rousseaux et al., in *Methods Enzymol.,* 121:663–669, Academic Press (1986).

Storb, *Blood* 68:119–125 (1986).

Storb and Thomas, *Immunol. Rev.* 88:215–238 (1985).

Freireich E.J., et al. (Quantitative Comparison of Toxicity of Anticancer Agents in Mouse, Rat, Hamster, Dog, Monkey, and Man. Cancer Chemother, Rep. 50, No. 4, 219–244, May 1966).

Seed and Aruffo (*Proc. Natl. Acad. Sci.* 84:3365 1987.

Linsley et al., *Proc. Natl. Acad.* Sci. USA 87:5031 (1990).

Hansen et al., *Immunogenetics* 10:247 (1980).

Ledbetter et al., *Proc. Natl. Acad. Sci.* 84:1384–1388 (1987).

Ledbetter et al., *Blood* 75:1531 (1990).

Wysocki and Sato, *Proc Natl. Acad. Sci.* 75:2844 (1978).

Volkman et al., *Proc. Natl. Acad. Sci. USA* 78:2528 (1981).

Vitetta et al., *J. Exp. Med.* 134:242 (1971).

Damle et al., *J. Immunol.* 140:1753–1761 (1988).

Schnek et al., *Cell* 56:47 (1989).

Recny et al., *J. Biol. Chem.* 265:8542 (1990).

Clayton et al., *Nature* 339:548 (1988).

Alzari et al., *Ann. Rev. Immuno.* 6:555 (1988).

June et al., *Immunology Today* 11:211 (1989).

C. Ricordi et al. Transplantation 52:519 (1991).

A.G. Tzakis et al. Lancet 336:402 (1990).

C. Ricordi, P.E. Lacy, E. H. Finke, B.J. Olack, D. W. Scharp, Diabetes 37:413 (1988).

D. Faustman and C. Coe, Science 252:1700 (1991).

Y. J. Zeng et al. Transplantation 53:277 (1992).

S. M. Hsu, L. Raine, H. Fanger, J. Histochem, Cytochem, 29:577 (1981).

P. S. Linsley et al., Science 257:792 (1992).

T. Yokochi, R. D. Holly, E. A. Clark, J. Immunol. 128:823 (1982).

Ohara, J., and W. E. Paul 1985, Production of a monoclonal antibody to and molecular characterization of B–Cell stimulatory factor–1 Nature 315:333) (Verax (Lebanon, NH)).

William C. Fanslow et al. "Regulation of Alloreactivity in vivo by IL–4 and the soluble I1–4 receptor"J. Immunol. 147:535–540 (1991).

J. Cohen Science 257:751 Aug. 7, 1992.
D.J. Lenschow et al. Science 257:789 Aug. 7, 1992.
L.A. Turka et al. PNAS 89:11102–5 Nov. 1992.
C.R. Maliszewski et al. Cell Immunol. 143:434–448 Sep. 1992.

J.M. Doutrelepont et al. Clin. Exp. Immunol. 83: 133–136 1991.

S.P. Umland et al. Clin. Immunol & Immunopath. 63:66 1992.

FIG. 3

ONCOSTATIN M SIGNAL PEPTIDE

```
     -25                    -20
      M   G   V   L   L   T   Q   R   T   L   L   S   L   V   L
     ATG GGT GTA CTG CTC ACA CAG AGG ACG CTG CTC AGT CTG GTC CTT    45

-10                                      -1 +1
      A   L   L   F   P   S   M   A   S   M   A   M   H   V   A
     GCA CTC CTG TTT CCA AGC ATG GCG AGC ATG GCA ATG CAC GTG GCC    90

+10                                  +20
      Q   P   A   V   V   L   A   S   S   R   G   I   A   S   F
     CAG CCT GCT GTG GTA CTG GCC AGC AGC CGA GGC ATC GCC AGC TTT   135

+30
      V   C   E   Y   A   S   P   G   K   A   T   E   V   R   V
     GTG TGT GAG TAT GCA TCT CCA GGC AAA GCC ACT GAG GTC CGG GTG   180

+40                                  +50
      T   V   L   R   Q   A   D   S   Q   V   T   E   V   C   A
     ACA GTC CTT CGG CAG GCT GAC AGC CAG GTG ACT GAA GTC TGT GCG   225

+60
      A   T   Y   M   M   G   N   E   L   T   F   L   D   D   S
     GCA ACC TAC ATG ATG GGG AAT GAG TTG ACC TTC CTA GAT GAT TCC   270

+70                                  +80
      I   C   T   G   T   S   S   G   N   Q   V   N   L   T   I
     ATC TGC ACG GGC ACC TCC AGT GGA AAT CAA GTG AAC CTC ACT ATC   315

+90
      Q   G   L   R   A   M   D   T   G   L   Y   I   C   K   V
     CAA GGA CTG AGG GCC ATG GAC ACG GGA CTC TAC ATC TGC AAG GTG   360

GLYCOSYLATION SITE
                        +100                                 +110
      E   L   M   Y   P   P   P   Y   Y   L   G   I   G   N   G
     GAG CTC ATG TAC CCA CCG CCA TAC TAC CTG GGC ATA GGC AAC GGA   405

+120
      T   Q   I   Y   V   I   D   P   E   P   C   P   D   S   D
     ACC CAG ATT TAT GTA ATT GAT CCA GAA CCG TGC CCA GAT TCT GAC   450

+130
      F   L   L   W   I   L   A   A   V   S   G   L   F   F
     TTC CTC CTC TGG ATC CTT GCA GCA GTT AGT TCG GGG TTG TTT TTT   495

+140                                 +150
      Y   S   F   L   L   T   A   V   S   L   S   K   M   L   K
     TAT AGC TTT CTC CTC ACA GCT GTT TCT TTG AGC AAA ATG CTA AAG   540

+160
      K   R   S   P   L   T   T   G   V   Y   V   K   M   P   P
     AAA AGA AGC CCT CTT ACA ACA GGG GTC TAT GTG AAA ATG CCC CCA   585

+170                                 +180
      T   E   P   E   C   E   K   Q   F   Q   P   Y   F   I   P
     ACA GAG CCA GAA TGT GAA AAG CAA TTT CAG CCT TAT TTT ATT CCC   630

+187
      I   N
     ATC AAT                                                       636
```

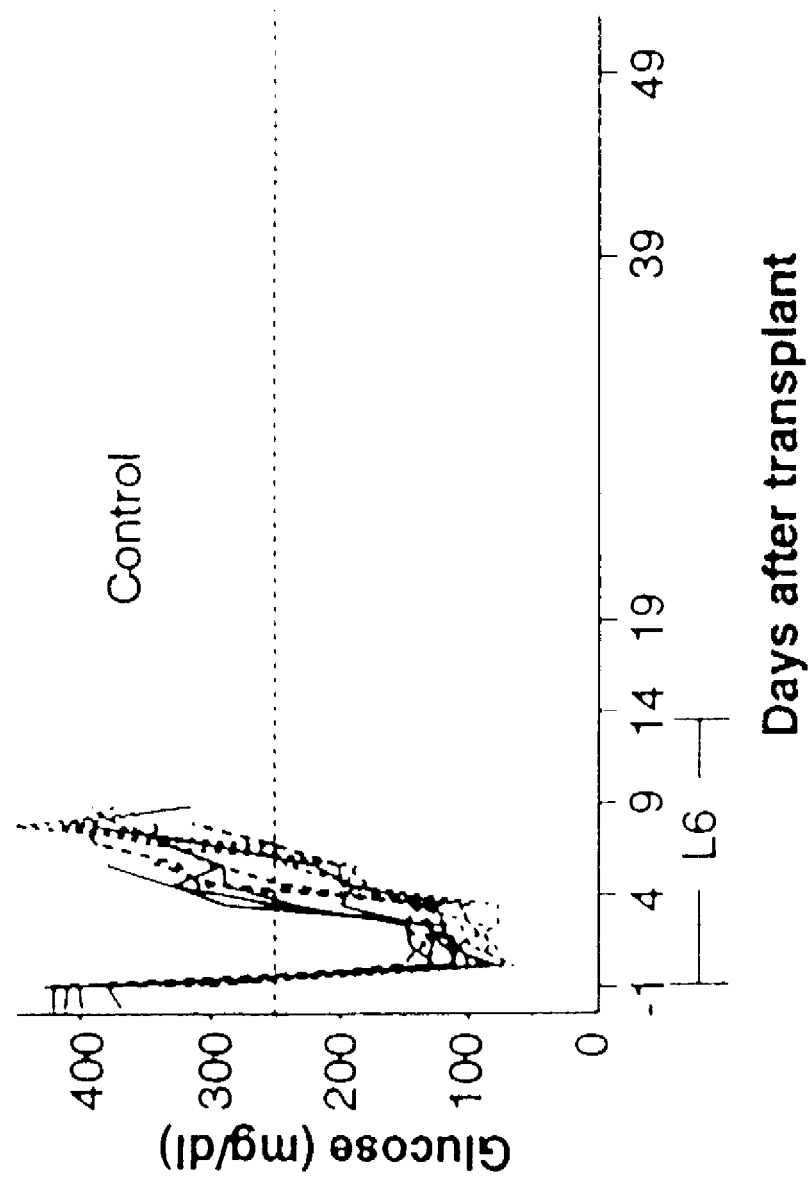

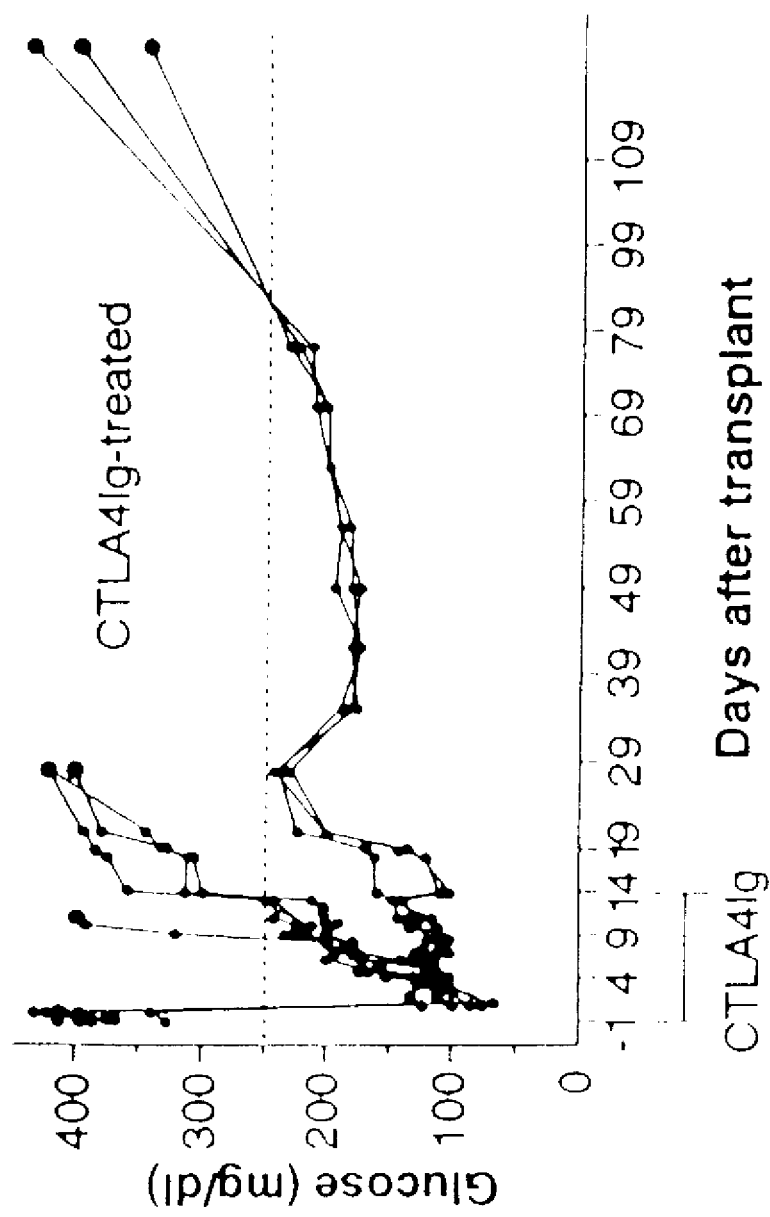

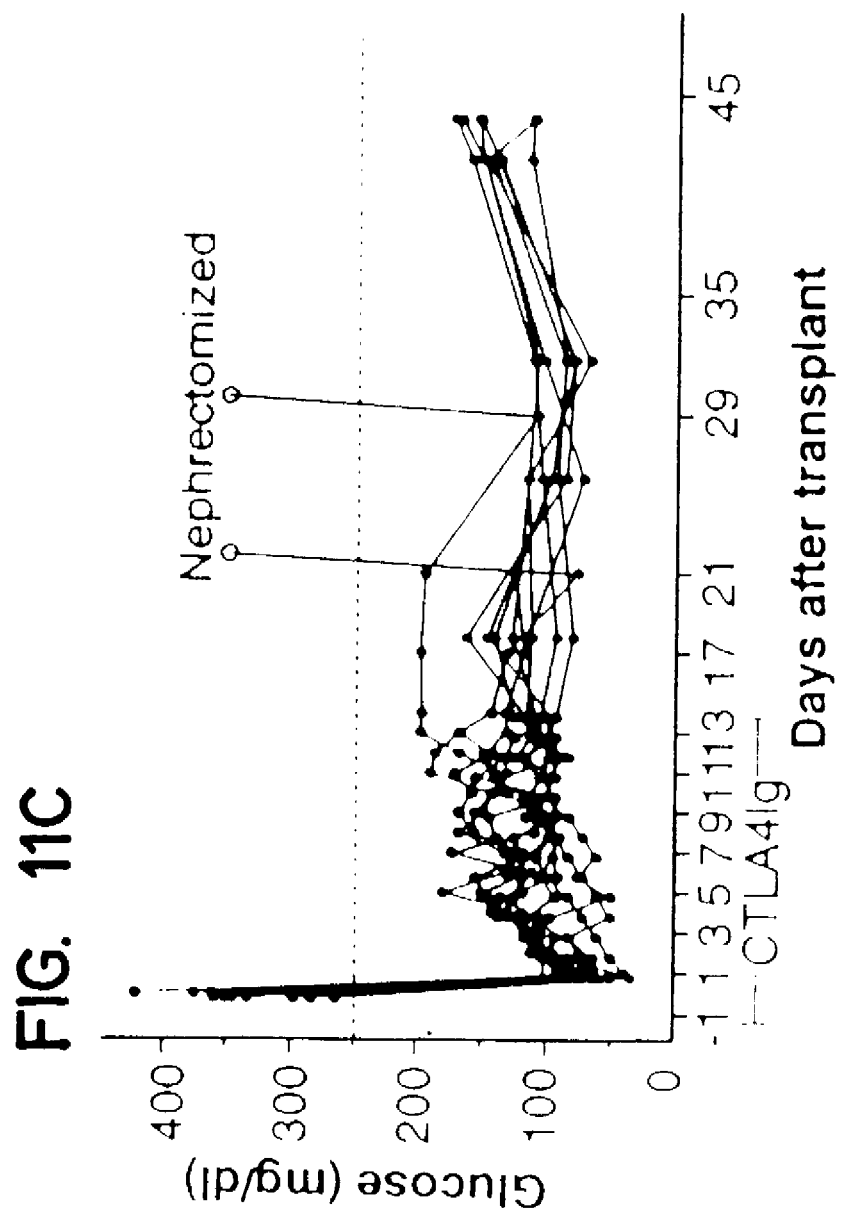

METHODS FOR REGULATING THE IMMUNE RESPONSE USING B7 BINDING MOLECULES AND IL4-BINDING MOLECULES

This application is a continuation-in-part of U.S. Ser. No. 723,617, filed Jul. 27, 1991, the contents of which are incorporated by reference into the present application Throughout this application various publications are referenced. The disclosures of these publications in their entireties are hereby incorporated by reference into this application in order to more fully describe the state of the art to which this invention pertains.

The present invention relates to expression of the CTLA4 receptor gene, identification of the interaction between the receptor and cells expressing B7 antigen, and to methods for regulating cellular interactions involving the CTLA4 receptor and the B7 antigen.

BACKGROUND OF THE INVENTION

The hallmark of a vertebrate immune system is the ability to discriminate "self" from "non-self" (foreign). This property has led to the evolution of a system requiring multiple signals to achieve optimal immune activation (Janeway, *Cold Spring Harbor Symp. Quant. Biol.* 54:1–14 (1989)). T cell-B cell interactions are essential to the immune response. Levels of many cohesive molecules found on T cells and B cells increase during an immune response (Springer et al., (1987), supra; Shaw and Shimuzu, *Current Opinion in Immunology*, Eds. Kindt and Long, 1:92–97 (1988)); and Hemler *Immunology Today* 9:109–113 (1988)). Increased levels of these molecules may help explain why activated B cells are more effective at stimulating antigen-specific T cell proliferation than are resting B cells (Kaiuchi et al., *J. Immunol.* 131:109–114 (1983); Kreiger et al., *J. Immunol.* 135:2937–2945 (1985); McKenzie, *J. Immunol.* 141:2907–2911 (1988); and Hawrylowicz and Unanue, *J. Immunol.* 141:4083–4088 (1988)).

The generation of a T lymphocyte ("T cell") immune response is a complex process involving cell-cell interactions (Springer et al., *A. Rev. Immunol.* 5:223–252 (1987)), particularly between T and accessory cells such as B cells, and production of soluble immune mediators (cytokines or lymphokines) (Dinarello and Mier, *New Engl. Jour. Med* 317:940–945 (1987)). This response is regulated by several T-cell surface receptors, including the T-cell receptor complex (Weiss et al., *Ann. Rev. Immunol.* 4:593–619 (1986)) and other "accessory" surface molecules (Springer et al., (1987) supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y. (1987)).

Antigen-independent intercellular interactions involving lymphocyte accessory molecules are essential for an immune response (Springer et al., (1987), supra). For example, binding of the T cell-associated protein, CD2, to its ligand LFA-3, a widely expressed glycoprotein (reviewed in Shaw and Shimuzu, supra), is important for optimizing antigen-specific T cell activation (Moingeon et al., *Nature* 339:314 (1988)).

An important adhesion system involves binding of the LFA-1 glycoprotein found on lymphocytes, macrophages, and granulocytes (Springer et al., (1987), supra; Shaw and Shimuzu (1988), supra) to its ligands ICAM-1 (Makgoba et al., *Nature* 331:86–88 (1988)) and ICAM-2 (Staunton et al., *Nature* 339:61–64 (1989)). The T cell accessory molecules CD8 and CD4 strengthen T cell adhesion by interaction with MHC class I (Norment et al., *Nature* 336:79–81 (1988)) and class II (Doyle and Strominger, *Nature* 330:256–259 (1987)) molecules, respectively. "Homing receptors" are important for control of lymphocyte migration (Stoolman, *Cell* 56:907–910 (1989)).

The VLA glycoproteins are integrins which appear to mediate lymphocyte functions requiring adhesion to extracellular matrix components (Hemler, supra). The CD2/LFA-3, LFA-1/ICAM-1 and ICAM-2, and VLA adhesion systems are distributed on a wide variety of cell types (Springer et al., (1987), supra; Shaw and Shimuzu, (1988,) supra and Hemler, (1988), supra).

Numerous in vitro studies have demonstrated that cytokines are involved in the generation of alloreactive effector cells. For example, membrane bound IL-4 and soluble IL-4 receptor were administered separately to mice and were shown to augment the lymphoproliferative response (William C. Fanslow et al. "Regulation of Alloreactivity in vivo by IL-4 and the soluble Il-4 receptor" *J. Immunol.* 147:535–540 (1991)). Specifically, administration of IL-4 to BALB\c mice resulted in slight augmentation of the lymphoproliferative response. In contrast, the soluble IL-4 receptor suppressed this response to allogeneic cells in a dose dependent manner. Moreover, a neutralizing antibody against IL-4 and another against soluble IL-4 receptor were effective inhibitors of the lymphoproliferative response.

It was proposed many years ago that B lymphocyte activation requires two signals (Bretscher and Cohn, *Science* 169:1042–1049 (1970)) and now it is believed that all lymphocytes require two signals for their optimal activation, an antigen specific or clonal signal, as well as a second, antigen non-specific signal (Janeway, supra). Freeman et al. (*J. Immunol.* 143(8):2714–2722 (1989)) isolated and sequenced a cDNA clone encoding a B cell activation antigen recognized by mAb B7 (Freeman et al., *J. Immunol.* 138:3260 (1987)). COS cells transfected with this cDNA have been shown to stain by both labeled mAb B7 and mAb BB-1 (Clark et al., *Human Immunol.* 16:100–113 (1986); Yokochi et al., *J. Immunol.* 128:823 (1981)); Freeman et al., (1989) supra; and Freedman et al., (1987), supra)). In addition, expression of this antigen has been detected on cells of other lineages, such as monocytes (Freeman et al., supra).

The signals required for a T helper cell ($T_h$) antigenic response are provided by antigen-presenting cells (APC). The first signal is initiated by interaction of the T cell receptor complex (Weiss, *J. Clin. Invest.* 86:1015 (1990)) with antigen presented in the context of class II major histocompatibility complex (MHC) molecules on the APC (Allen, *Immunol. Today* 8:270 (1987)). This antigen-specific signal is not sufficient to generate a full response, and in the absence of a second signal may actually lead to clonal inactivation or anergy (Schwartz, *Science* 248:1349 (1990)). The requirement for a second "costimulatory" signal provided by the MHC has been demonstrated in a number of experimental systems (Schwartz, supra; Weaver and Unanue, *Immunol. Today* 11:49 (1990)). The molecular nature of this second signal(s) is not completely understood, although it is clear in some cases that both soluble molecules such as interleukin (IL)-1 (Weaver and Unanue, supra) and membrane receptors involved in intercellular adhesion (Springer, *Nature* 346:425 (1990)) can provide costimulatory signals.

CD28 antigen, a homodimeric glycoprotein of the immunoglobulin superfamily (Aruffo and Seed, *Proc. Natl. Acad.*

Sci. 84:8573–8577 (1987)), is an accessory molecule found on most mature human T cells (Damle et al., *J. Immunol.* 131:2296–2300 (1983)). Current evidence suggests that this molecule functions in an alternative T cell activation pathway distinct from that initiated by the T-cell receptor complex (June et al., *Mol. Cell. Biol.* 7:4472–4481 (1987)). Monoclonal antibodies (mAbs) reactive with CD28 antigen can augment T cell responses initiated by various polyclonal stimuli (reviewed by June et al., supra). These stimulatory effects may result from mAb-induced cytokine production (Thompson et al., *Proc. Natl. Acad. Sci* 86:1333–1337 (1989); and Lindsten et al., *Science* 244:339–343 (1989)) as a consequence of increased mRNA stabilization (Lindsten et al., (1989), supra). Anti-CD28 mAbs can also have inhibitory effects, i.e., they can block autologous mixed lymphocyte reactions (Damle et al., *Proc. Natl. Acad. Sci.* 78:5096–6001 (1981)) and activation of antigen-specific T cell clones (Lesslauer et al., *Eur. J. Immunol.* 16:1289–1296 (1986)).

Studies have shown that CD28 is a counter-receptor for the B cell activation antigen, B7/BB-1 (Linsley et al, *Proc. Natl. Acad. Sci. USA* 87:5031–5035 (1990)). For convenience the B7/BB-1 antigen is hereafter referred to as the "B7 antigen".

Interactions between CD28 and B7 antigen have been characterized using genetic fusions of the extracellular portions of B7 antigen and CD28 receptor, and Immunoglobulin (Ig) Cγ1 (constant region heavy chains) (Linsley et al, *J. Exp. Med.* 173:721–730 (1991)). Immobilized B7Ig fusion protein, as well as B7 positive CHO cells, have been shown to costimulate T cell proliferation.

T cell stimulation with B7 positive CHO cells also specifically stimulates increased levels of transcripts for IL-2. Additional studies have shown that anti-CD28 mAb inhibited IL-2 production induced in certain T cell leukemia cell lines by cellular interactions with a B cell leukemia line (Kohno et al., *Cell. Immunol.* 131-1-10 (1990)).

CD28 has a single extracellular variable region (V)-like domain (Aruffo and Seed, supra). A homologous molecule, CTLA4 has been identified by differential screening of a murine cytolytic-T cell cDNA library (Brunet et al., *Nature* 328:267–270 (1987)).

Transcripts of the CTLA4 molecule have been found in T cell populations having cytotoxic activity, suggesting that CTLA4 might function in the cytolytic response (Brunet et al., supra; and Brunet et al., *Immunol. Rev.* 103-21-36 (1988)). Researchers have reported the cloning and mapping of a gene for the human counterpart of CTLA4 (Dariavach et al., *Eur. J. Immunol.* 18:1901–1905 (1988)) to the same chromosomal region (2q33-34) as CD28 (Lafage-Pochitaloff et al., *Immunogenetics* 31:198–201 (1990)).

Sequence comparison between this human CTLA4 DNA and that encoding CD28 proteins reveals significant homology of sequence, with the greatest degree of homology in the juxtamembrane and cytoplasmic regions (Brunet et al., 1988, supra; Dariavach et al., 1988, supra).

The high degree of homology between CD28 and CTLA4, together with the co-localization of their genes, raises questions as to whether these molecules are also functionally related. However, since the protein product of CTLA4 has not yet been successfully expressed, these questions remain unanswered.

Expression of soluble derivatives of cell-surface glycoproteins in the immunoglobulin gene superfamily has been achieved for CD4, the receptor for HIV-1, and CD28 and B7 receptors, using hybrid fusion molecules consisting of DNA sequences encoding amino acids corresponding to portions of the extracellular domain of CD4 receptor fused to antibody domains (immunoglobulin γ1 (Capon et al., *Nature* 337:525–531 (1989) (CD4) and Linsley et al., *J. Exp. Med.*, supra (CD28 and B7)).

There is a need for the present invention. At present, the major therapies to prevent the rejection of organ transplants rely on panimmunosuppressive drugs, such as cyclosporine A or monoclonal antibodies (MAbs) to CD3. These drugs must frequently be taken for the life of the individual, depress the entire immune system, and often result in secondary health ailments such as increased frequency of infections and cancer.

SUMMARY OF THE INVENTION

Accordingly, the present invention provides the complete and correct DNA sequence encoding the amino acid sequence corresponding to the CTLA4 receptor protein, and identifies B7 antigen as a natural ligand for the CTLA4 receptor. The invention also provides a method for expressing the DNA as a CTLA4 immunoglobulin (Ig) fusion protein product. Embodiments of the invention include CTLA4Ig fusion protein, and hybrid fusion proteins including CD28Ig/CTLA4Ig fusion proteins. Also provided are methods for using the CTLA4 fusion protein, B7Ig fusion protein, hybrid fusion proteins, and fragments and/or derivatives thereof, such as monoclonal antibodies reactive with CTLA4 and the B7 antigen, to regulate cellular interactions and immune responses.

The human CTLA receptor protein of the invention is encoded by 187 amino acids and includes a newly identified N-linked glycosylation site.

The CTLA4Ig fusion protein of the invention binds the B7 antigen expressed on activated B cells, and cells of other lineages, a ligand for CD28 receptor on T cells. The CTLA4Ig binds B7 antigen with significantly higher affinity than B7 binding to the CD28 receptor. The CTLA4Ig construct has a first amino acid sequence corresponding to the extracellular domain of the CTLA4 receptor fused to a second amino acid sequence corresponding to the human Ig Cγ1 domain. The first amino acid sequence contains amino acid residues from about position 1 to about position 125 of the amino acid sequence corresponding to the extracellular domain of CTLA4 joined to a second amino acid sequence containing amino acid residues corresponding to the hinge, CH2 and CH3 regions of human IgCγ1. The fusion protein is preferably produced in dimeric form. Soluble CTLA4Ig is a potent inhibitor in vitro of T and B lymphocyte responses.

Also contemplated in the invention are hybrid fusion proteins such as CD28Ig/CTLA4Ig fusion proteins having a first amino acid sequence corresponding to fragments of the extracellular domain of CD28 joined to a second amino acid sequence corresponding to fragments of the extracellular domain of CTLA4Ig and a third amino acid sequence corresponding to the hinge, CH2 and CH3 regions of human IgCγ1. One embodiment of the hybrid fusion proteins is a CD28Ig/CTLA4Ig fusion construct having a first amino acid sequence containing amino acid residues from about position 1 to about position 94 of the amino acid sequence corresponding to the extracellular domain of CD28, joined a second amino acid sequence containing amino acid residues from about position 94 to about position 125 of the amino acid sequence corresponding to the extracellular domain of CTLA4, joined to a third amino acid sequence containing amino acids residues corresponding to the hinge, CH2 and CH3 regions of human IgCγ1.

Also included in the invention is a method for regulating T cell interactions with other cells by inhibiting the interaction of CTLA4-positive T cells with B7 positive cells by reacting the T cells with ligands for the CTLA4 receptor. The ligands include B7Ig fusion protein, a monoclonal antibody reactive with CTLA4 receptor, and antibody fragments.

The invention also provides a method for regulating T cell interactions with B7 positive cells, using a ligand for the B7 antigen. Such a ligand is the CTLA4Ig fusion protein of the invention, its fragments or derivatives, the CD28Ig/CTLA4Ig fusion protein hybrid, or a monoclonal antibody reactive with the B7 antigen.

The invention further includes a method for treating immune system diseases mediated by T cell interactions with B7 positive cells by administering a ligand reactive with B7 antigen to regulate T cell interactions with B7 positive cells. The ligand is the CTLA4Ig fusion protein, or the CD28Ig/CTLA4Ig fusion protein hybrid, or a monoclonal antibody reactive with B7 antigen.

A monoclonal antibody reactive with the CTLA4Ig fusion protein and a monoclonal antibody reactive with CD28Ig/CTLA4Ig fusion protein are described for use in regulating cellular interactions.

A novel Chinese Hamster Ovary cell line stably expressing the CTLA4Ig fusion protein is also disclosed.

Further, the present invention provides a method for blocking B7 interaction so as to regulate the immune response. This method comprises contacting lymphocytes with a CTLA4-binding molecule and an IL4-binding molecule.

Additionally, the present invention provides a method for regulating an immune response which comprises contacting B7-positive lymphocytes with a CTLA4-binding molecule and an IL4-binding molecule.

Also, the invention provides method for inhibiting tissue transplant rejection by a subject, the subject being a recipient of transplanted tissue. This method comprises administering to the subject a CTLA4-binding molecule and an IL4-binding molecule.

The present invention further provides a method for inhibiting graft versus host disease in a subject which comprises administering to the subject a CTLA4-binding molecule and an IL4-binding molecule.

BRIEF DESCRIPTION OF THE FIGURES

FIG. 3 depicts the complete amino acid sequence encoding human CTLA4 receptor (SEQ ID NOs: 13 and 14) fused to the oncostatin M signal peptide (position −25 to −1), and including the newly identified N-linked glycosylation site (position 109–111), as described in Example 3, infra.

FIGS. 11A, 11B, and 11C are line graphs showing the survival of human pancreatic islet xenografts.

DETAILED DESCRIPTION OF THE INVENTION

Definition

Figure 1:
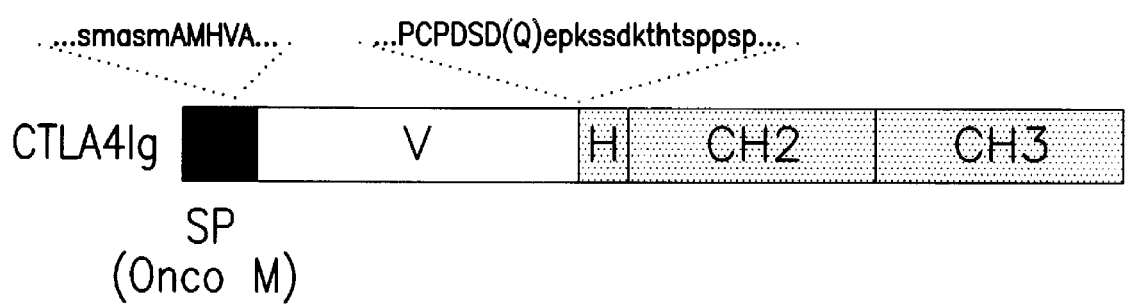
FIG. 1 is a diagrammatic representation of CTLA4Ig fusion constructs as described in Example 2, infra.

As used in this application, the following words or phrases have the meanings specified.

As used herein "blocking B7 interaction" means to interfere with the binding of the B7 antigen to its ligands such as CD28 and CTLA4 thereby obstructing T cell and B cell interaction.

As used herein a "B7-binding molecule" means any molecule which will bind the B7 antigen.

As used herein an "IL4-binding molecule" means any molecule which will recognize and bind to IL4.

In order that the invention herein described may be more fully understood, the following description is set forth.

This invention is directed to the isolation and expression of the human CTLA4 receptor found on T cell surfaces, which binds to the B7 antigen expressed on activated B cells, and cells of other lineages, and to expression of soluble fusion protein products of the CTLA4 receptor gene. The invention also provides methods for using the expressed CTLA4 receptor to regulate cellular interactions, including T cell interactions with B7 positive cells.

In a preferred embodiment, the complete and correct DNA sequence encoding the amino acid sequence corresponding to human CTLA4 receptor protein of the invention is cloned using PCR. The cDNA containing the complete predicted coding sequence of CTLA4 was assembled from two PCR fragments amplified from H38 RNA, and inserted into the expression vector, CDM8 as described in detail in the Examples, infra. Isolates were transfected into COS cells and tested for binding of B7Ig, a soluble fusion protein having an amino acid sequence corresponding to the extracellular domain of B7 and a human immunoglobulin (Ig) $C\gamma 1$ region, as described by Linsley et al., *J. Exp. Med.* 173:721–730 (1991).

The DNA sequence of one isolate, designated as OMCTLA4, was then determined and found to correspond exactly to the predicted human CTLA4 sequence, fused at the N-terminus to the signal peptide from oncostatin M. The CTLA4 receptor is encoded by 187 amino acids (exclusive of the signal peptide and stop codons) and includes a newly identified N-linked glycosylation site at amino acid positions 109–111 (see FIG. 3, infra). The CTLA4 receptor is expressed using the oncostatin M signal peptide.

In another preferred embodiment, soluble forms of the protein product of the CTLA4 receptor gene (CTLA4Ig) are prepared using fusion proteins having a first amino acid sequence corresponding to the extracellular domain of CTLA4 and a second amino acid sequence corresponding to the human IgC$\gamma$1 domain. Cloning and expression plasmids (CDM8 and $\pi$LN) were constructed containing cDNAs encoding portions of the amino acid sequence corresponding to human CTLA4 receptor based on the cDNA sequence described herein, where the cDNA encoding a first amino acid sequence corresponding to a fragment of the extracellular domain of the CTLA4 receptor gene is joined to DNA encoding a second amino acid sequence corresponding to an IgC region that permits the expression of the CTLA4 receptor gene by altering the solubility of the expressed CTLA4 protein. Thus, soluble CTLA4Ig fusion protein is encoded by a first amino acid sequence containing amino acid residues from about position 1 to about position 125 of the amino acid sequence corresponding to the extracellular domain of CTLA4 joined to a second amino acid sequence containing amino acid residues corresponding to the hinge, CH2 and CH3 regions of human IgC$\gamma$1. The fusion protein is preferably produced in dimeric form. The construct was then transfected into COS or CHO cells, and CTLA4Ig was purified and identified as a dimer.

In accordance with the practice of this invention, CTLA4Ig and the CTL4Ig/CD28 fusion protein hybrid may have amino acid substitutions in the amino acid sequence corresponding to the external domain of CTLA4 so as to produce molecules which would retain the functional property of CTLA4, namely, the molecule having such substitutions will still bind the B7 antigen. These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

In fact, using the methodologies disclosed herein, mutants of the CTLA4-binding molecule were produced. One mutant comprises (1) a sequence beginning with the amino acid at position 1 and ending with the amino acid at position 95 of the CD28 receptor protein (Aruffo and Seed 1987); (2) a sequence beginning with the amino acid at position 95 and ending with amino acid at position 125 of the extracellular domain of CTLA4 (Brunet et al. 1987); and (3) a sequence corresponding to the human IgC$\gamma$1 domain.

The second mutant comprises (1) a sequence beginning with the amino acid at position 1 and ending with the amino acid at position 95 of the CD28 receptor protein (Aruffo and Seed 1987); (2) a sequence beginning with the amino acid at position 95 and ending with amino acid at position 120 of the extracellular domain of CTLA4 (Brunet et al. 1987); and (3) a sequence corresponding to the human IgC$\gamma$1 domain.

The present invention provides a method for blocking B7 interaction so as to regulate the immune response which comprises contacting lymphocytes with a B7-binding molecule and an IL4-binding molecule. The lymphocytes may be B7 positive lymphocytes.

Further, the present invention provides a method for regulating an immune response which comprises contacting B7-positive lymphocytes with a B7-binding molecule and an IL4-binding molecule.

The immune response may be a B cell response resulting in the inhibition of antibody production. Additionally, the immune response may be a T cell response resulting in inhibition of cell mediated immunity. Further, the immune response may be an inhibition of lymphocyte proliferation.

Also, the present invention provides a method for inhibiting tissue transplant rejection by a subject, the subject being a recipient of transplanted tissue. This method can comprise administering to the subject a CTLA4-binding molecule and an IL4-binding molecule.

The invention further provides a method for inhibiting graft versus host disease in a subject which comprises administering to the subject a CTLA4-binding molecule and an IL4-binding molecule.

In accordance with the practice of this invention, the CTLA4-binding molecule may be a CTLA4Ig fusion protein. For example, the CTLA4Ig fusion protein may be a fusion protein having a first amino acid sequence containing amino acid residues from about position 1 to about position 125 of the amino acid sequence corresponding to the extracellular domain of CTLA4 and a second amino acid sequence containing amino acid residues corresponding to the hinge, CH2 and CH3 regions of human immunoglobulin Cγ1.

Alternatively, the CTLA4-binding molecule may be a CD28Ig/CTLA4Ig fusion protein hybrid. For example, the CD28Ig/CTLA4Ig fusion protein hybrid may be a fusion protein hybrid having a first amino acid sequence corresponding to a portion of the extracellular domain of CD28 receptor fused to a second amino acid sequence corresponding to a portion of the extracellular domain of CTLA4 receptor and a third amino acid sequence corresponding to the hinge, CH2 and CH3 regions of human immunoglobulin Cγ1.

Further, the IL4-binding molecule may be a monoclonal antibody which specifically recognizes and binds to IL4. Alternatively, the IL4-binding molecule is a soluble IL4 receptor which recognizes and binds to IL4 (Fanslow et al. 1991).

DNA encoding the amino acid sequence corresponding to the CTLA4Ig fusion protein has been deposited with the American Type Culture Collection (ATCC) in Rockville, Md., under the provisions of the Budapest Treaty on May 31, 1991 and has been accorded ATCC accession number: 68629.

The present invention provides the first protein product of CTLA4 transcripts in the form of a soluble fusion protein. The CTLA4Ig protein forms a disulfide-linked dimer having two subunits, each of which has an $M_r$ of approximately 50,000 indicating that native CTLA4 probably exists on the T cell surface as a disulfide-linked homodimer.

B7 antigen has been shown to be a ligand for CD28 receptor on T cells (Linsley et al., Proc. Natl. Acad. Sci. USA, supra). The CTLA4 receptor molecule appears functionally and structurally related to the CD28 receptor; both are receptors for the B cell activation antigen, B7, while CTLA4 appears to have higher affinity for B7, among the highest yet reported for lymphoid adhesion systems. However, CTLA4Ig was shown to bind more strongly to B7 positive (B7$^+$) cell lines than CD28Ig. Other experiments demonstrated that CTLA4 is a higher affinity receptor for B7 antigen than CD28 receptor. Additionally, CTLA4Ig was shown to bind a single protein on lymphoblastoid cells which is similar in size to the B7 antigen. CTLA4Ig inhibited T cell proliferation and inhibited $T_h$-induced IgM production.

In another preferred embodiment, hybrid fusion proteins having amino acid sequences corresponding to fragments of different receptor proteins were constructed. For example, amino acid sequences corresponding to selected fragments of the extracellular domains of CD28 and CTLA4 were linked to form CD28Ig/CTLA4Ig hybrid fusion proteins. Thus, a CD28Ig/CTLA4Ig fusion protein was obtained having a first amino acid sequence containing amino acid residues corresponding to a fragment of the extracellular domain of CD28 joined to a second amino acid sequence corresponding to a fragment of the extracellular domain of CTLA4Ig and to a third amino acid sequence corresponding to the hinge, CH2 and CH3 regions of human IgCγ1. One embodiment of the hybrid fusion proteins is a CD28Ig/CTLA4Ig fusion construct having a first amino acid sequence containing amino acid residues from about position 1 to about position 94 of the amino acid sequence corresponding to the extracellular domain of CD28, joined to a second amino acid sequence containing amino acid residues from about position 94 to about position 125 of the amino acid sequence corresponding to the extracellular domain of CTLA4, joined to a third amino acid sequence corresponding to the hinge, CH2 and CH3 regions of human IgCγ1.

The techniques for cloning and expressing DNA sequences encoding the amino acid sequences corresponding to the CTLA4 receptor protein, soluble fusion proteins and hybrid fusion proteins, e.g synthesis of oligonucleotides, PCR, transforming cells, constructing vectors, expression systems, and the like are well-established in the art, and most practitioners are familiar with the standard resource materials for specific conditions and procedures. However, the following paragraphs are provided for convenience and notation of modifications where necessary, and may serve as a guideline.

Cloning and Expression of Coding Sequences for Receptors and Fusion Proteins

Fusion protein constructs corresponding to CD28IgCγ1 and B7IgCγ1 for characterizing the CTLA4Ig of the present invention, and for preparing CD28Ig/CTLA4Ig fusion hybrids, were prepared as described by Linsley et al., J. Exp. Med. 173:721–730 (1991), incorporated by reference herein. Alternatively, cDNA clones may be prepared from RNA obtained from cells expressing B7 antigen and CD28 receptor based on knowledge of the published sequences for these proteins (Aruffo and Seed, and Freeman, supra) using standard procedures.

CTLA4Ig fusions consisting of DNA encoding amino acid sequences corresponding to the extracellular domain of CTLA4 and the hinge, CH2 and CH3 regions of human IgCγ1 were constructed by ligation of PCR fragments. The cDNA encoding the amino acid sequences is amplified using the polymerase chain reaction ("PCR") technique (see U.S. Pat. Nos. 4,683,195 and 4,683,202 to Mullis et al. and Mullis & Faloona, Methods Enzymol. 154:335–350 (1987)). CTLA4Ig fusion polypeptides were obtained having DNA encoding amino acid sequences containing amino acid residues from about position 1 to about position 125 of the amino acid sequence corresponding to the extracellular domain of CTLA4 and DNA encoding amino acid sequences corresponding to the hinge, CH2 and CH3 regions of Ig Cγ1.

Because the expression of CTLA4 receptor protein in human lymphoid cells has not been previously reported, it was necessary to locate a source of CTLA4 mRNA. PCR cDNA made from the total cellular RNA of several human leukemia cell lines was screened, using as primers, oligonucleotides from the published sequence of the CTLA4 gene (Dariavach et al., supra). Of the cDNA tested, H38 cells (an HTLV II-associated leukemia line) provided the best yield of PCR products having the expected size. Since a signal peptide for CTLA4 was not identified in the CTLA4 gene, the N terminus of the predicted sequence of CTLA4 was fused to the signal peptide of oncostatin M (Malik et al., Molec. and Cell. Biol. 9:2847 (1989)) in two steps using oligonucleotides as described in the Examples, infra. The product of the PCR reaction was ligated with cDNA encoding the amino acid sequences corresponding to the hinge, CH2 and CH3 regions of Ig Cγ1 into a expression vector, such as CDM8 or πLN.

To obtain DNA encoding full length human CTLA4, a cDNA encoding the transmembrane and cytoplasmic domains of CTLA4 was obtained by PCR from H38 cells and joined with a fragment from CTLA4Ig, obtained as described above, encoding the oncostatin M signal peptide fused to the N terminus of CTLA4, using oligonucleotide primers as described in the Examples, infra. PCR fragments were ligated into the plasmid CDM8, resulting in an expression plasmid encoding the full length CTLA4 gene, and designated OMCTLA4.

For construction of DNA encoding the amino acid sequence corresponding to hybrid fusion proteins, DNA encoding amino acids corresponding to portions of the extracellular domain of one receptor gene is joined to DNA encoding amino acids corresponding to portions of the extracellular domain of another receptor gene, and to DNA encoding the amino acid sequences corresponding to the hinge, CH2 and CH3 regions of human IgCγ1 using procedures as described above for the B7Ig, CD28Ig and CTLA4Ig constructs. Thus, for example, DNA encoding amino acid residues from about position 1 to about position 94 of the amino acid sequence corresponding to the extracellular domain of the CD28 receptor is joined to DNA encoding amino acid residues from about position 94 to about position 125 of the amino acid sequence corresponding to the extracellular domain of the CTLA4 receptor and to DNA encoding the amino acid sequences corresponding to the hinge, CH2 and CH3 regions of human IgCγ1.

To produce large quantities of cloned DNA, vectors containing DNA encoding the fusion constructs of the invention are transformed into suitable host cells, such as the bacterial cell line *E. coli* strain MC1061/p3 (Invitrogen Corp., San Diego, Calif.) using standard procedures, and colonies are screened for the appropriate plasmids.

The clones containing DNA encoding fusion constructs obtained as described above are then transfected into suitable host cells for expression. Depending on the host cell used, transfection is performed using standard techniques appropriate to such cells. For example, transfection into mammalian cells is accomplished using DEAE-dextran mediated transfection, CaPO$_4$ co-precipitation, lipofection, electroporation, or protoplast fusion, and other methods known in the art including: lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Expression in eukaryotic host cell cultures derived from multicellular organisms is preferred (see *Tissue Cultures*, Academic Press, Cruz and Patterson, Eds. (1973)). These systems have the additional advantage of the ability to splice out introns and thus can be used directly to express genomic fragments. Useful host cell lines include Chinese hamster ovary (CHO), monkey kidney (COS), VERO and HeLa cells. In the present invention, cell lines stably expressing the fusion constructs are preferred.

Expression vectors for such cells ordinarily include promoters and control sequences compatible with mammalian cells such as, for example, CMV promoter (CDM8 vector) and avian sarcoma virus (ASV) (πLN vector). Other commonly used early and late promoters include those from Simian Virus 40 (SV 40) (Fiers, et al., *Nature* 273:113 (1973)), or other viral promoters such as those derived from polyoma, Adenovirus 2, and bovine papilloma virus. The controllable promoter, hMTII (Karin, et al., *Nature* 299:797–802 (1982)) may also be used. General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eukaryotes.

Although preferred host cells for expression of the fusion constructs include eukaryotic cells such as COS or CHO cells, other eukaryotic microbes may be used as hosts. Laboratory strains of *Saccharomyces cerevisiae*, Baker's yeast, are most used although other strains such as *Schizosaccharomyces pombe* may be used. Vectors employing, for example, the 2μ origin of replication of Broach, *Meth. Enz.* 101:307 (1983), or other yeast compatible origins of replications (see, for example, Stinchcomb et al., *Nature* 282:39 (1979)); Tschempe et al., *Gene* 10:157 (1980); and Clarke et al., *Meth. Enz.* 101:300 (1983)) may be used. Control sequences for yeast vectors include promoters for the synthesis of glycolytic enzymes (Hess et al., *J. Adv. Enzyme Reg.* 7:149 (1968); Holland et al., *Biochemistry* 17:4900 (1978)). Additional promoters known in the art include the CMV promoter provided in the CDM8 vector (Toyama and Okayama, *FEBS* 268:217–221 (1990); the promoter for 3-phosphoglycerate kinase (Hitzeman et al., *J. Biol. Chem.* 255:2073 (1980)), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* 198: 1056 (1977)), the tryptophan (trp) promoter system (Goeddel et al., *Nucleic Acids Res.* 8:4057 (1980)) and the lambda derived P$_L$ promoter and N-gene ribosome binding site (Shimatake et al., *Nature* 292:128 (1981)).

The nucleotide sequences encoding CD28Ig and CTLA4Ig proteins, and fusion hybrid proteins such as CD28Ig/CTLA4Ig, may be expressed in a variety of systems as set forth below. The cDNA may be excised by suitable restriction enzymes and ligated into suitable prokaryotic or eukaryotic expression vectors for such expression. Because CD28 and CTLA4 receptor proteins occur in nature as dimers, it is believed that successful expression of these proteins requires an expression system which permits these proteins to form as dimers. Truncated versions of these proteins (i.e. formed by introduction of a stop codon into the sequence at a position upstream of the transmembrane region of the protein) appear not to be expressed. The expression of CD28 and CTLA4 receptors as fusion proteins permits dimer formation of these proteins. Thus, expression of CTLA4 protein as a fusion product is preferred in the present invention.

A stable CHO line of the invention, designated Chinese Hamster Ovary Cell Line CTLA4Ig-24, is preferred for expression of CTLA4Ig and has been deposited with the ATCC under the terms of the Budapest Treaty on May 31, 1991, and accorded ATCC accession number 10762.

Expression of the CTLA4 receptor of the invention is accomplished transfecting a cell line such as COS cells, and detecting expression by binding of the CTLA4-transfected cells to a ligand for the CTLA4 receptor, for example by testing for binding of the cells to B7Ig fusion protein.

Sequences of the resulting constructs are confirmed by DNA sequencing using known procedures, for example as described by Sanger et al., *Proc. Natl. Acad. Sci. USA* 74:5463 (1977), as further described by Messing et al., *Nucleic Acids Res.* 9:309 (1981), or by the method of Maxam et al. *Methods Enzymol.* 65:499 (1980)).

Recovery of Protein Products

As noted above, CD28 and CTLA4 receptor genes are not readily expressed as mature proteins using direct expression of DNA encoding the truncated protein. To enable homodimer formation, DNA encoding the amino acid sequence corresponding to the extracellular domains of CD28 and CTLA4, and including the codons for a signal sequence such as that of oncostatin M in cells capable of appropriate processing, is fused with DNA encoding the amino acid sequence corresponding to the Fc domain of a naturally dimeric protein. Purification of these fusion protein products after secretion from the cells is thus facilitated using antibodies reactive with the anti-immunoglobulin portion of the fusion proteins. When secreted into the medium, the fusion protein product is recovered using standard protein purification techniques, for example by application to protein A columns.

USE

CTLA4Ig fusion protein and/or fragments of the fusion protein may be used to react with B7 positive cells, such as B cells, to regulate immune responses mediated by T cell interactions with the B7 antigen positive cells.

CTLA4Ig fusion protein and CTLA4Ig/CD28Ig hybrid proteins, and/or fragments and derivatives of these proteins, may also be used to react with B7 positive cells, including B cells, to regulate immune responses mediated by T cell dependent B cell responses. The term "fragment" as used herein means a portion of the amino acid sequence encoding the protein referred to as "CTLA4". A fragment of the CTLA4Ig fusion protein that may be used is a polypeptide having an amino acid sequence corresponding to some portion of the amino acid sequence corresponding to the CTLA4 receptor used to obtain the CTLA4Ig fusion protein as described herein.

The B7 antigen expressed on activated B cells and cells of other lineages, and the CD28 receptor expressed on T cells, can directly bind to each other, and this interaction can mediate cell-cell interaction. Such interactions directly trigger the CD28 activation pathway in T cells, leading to cytokine production, T cell proliferation, and B cell differentiation into immunoglobulin producing cells. The activation of B cells that occurs, can cause increased expression of B7 antigen and further CD28 stimulation, leading to a state of chronic inflammation such as in autoimmune diseases, allograft rejection, graft versus host disease or chronic allergic reactions. Blocking or inhibiting this reaction may be effective in preventing T cell cytokine production and thus preventing or reversing inflammatory reactions.

CTLA4Ig is shown herein to be a potent inhibitor of in vitro lymphocyte functions requiring T and B cell interaction. This indicates the importance of interactions between the B7 antigen and its counter-receptors, CTLA4 and/or CD28. The cytoplasmic domains of murine and human CTLA4 are similar (Dariavach et al., supra, 1988), suggesting that this region has important functional properties. The cytoplasmic domains of CD28 and CTLA4 also share homology.

CTLA4 is a more potent inhibitor in vitro of lymphocyte responses than either anti-BB1, or anti-CD28 mAbs. CTLA4Ig does not have direct stimulatory effects on T cell proliferation to counteract its inhibitory effects. Therefore, the CTLA4Ig fusion protein may perform as a better inhibitor in vivo than anti-CD28 monoclonal antibodies. The immunosuppressive effects of CTLA4Ig in vitro suggests its use in therapy for treatment of autoimmune disorders involving abnormal T cell activation or Ig production.

The CTLA4Ig fusion protein is expected to exhibit inhibitory properties in vivo. Thus, it is expected that CTLA4Ig will act to inhibit T cells in a manner similar to the effects observed for the anti-CD28 antibody, under similar conditions in vivo. Under conditions where T cell/B cell interactions are occurring as a result of contact between T cells and B cells, binding of introduced CTLA4Ig to react with B7 antigen positive cells, for example B cells, may interfere, i.e. inhibit, the T cell/B cell interactions resulting in regulation of immune responses. Because of this exclusively inhibitory effect, CTLA4Ig is expected to be useful in vivo as an inhibitor of T cell activity, over non-specific inhibitors such as cyclosporine and glucosteroids.

In one embodiment, the CTLA4Ig fusion protein or CTLA4Ig/CD28Ig hybrid proteins, may be introduced in a suitable pharmaceutical carrier in vivo, i.e. administered into a human subject for treatment of pathological conditions such as immune system diseases or cancer.

Introduction of the fusion protein in vivo is expected to result in interference with T cell interactions with other cells, such as B cells, as a result of binding of the ligand to B7 positive cells. The prevention of normal T cell interactions may result in decreased T cell activity, for example, decreased T cell proliferation. In addition, administration of the fusion protein in vivo is expected to result in regulation of in vivo levels of cytokines, including, but not limited to, interleukins, e.g. interleukin ("IL")-2, IL-3, IL-4, IL-6, IL-8, growth factors including tumor growth factor ("TGF"), colony stimulating factor ("CSF"), interferons ("IFNs"), and tumor necrosis factor ("TNF") to promote desired effects in a subject. For example, when the fusion protein is introduced in vivo, it may block production of cytokines, which contribute to malignant growth, for example of tumor cells. The fusion protein may also block proliferation of viruses dependent on T cell activation, such as the virus that causes AIDS, HTLV1.

Under some circumstances, as noted above, the effect of administration of the CTLA4Ig fusion protein or its fragments in vivo is inhibitory, resulting from blocking by the fusion protein of the CTLA4 and CD28 triggering resulting from T cell/B cell contact. For example, the CTLA4Ig protein may block T cell proliferation. Introduction of the CTLA4Ig fusion protein in vivo will thus produce effects on both T and B cell-mediated immune responses. The fusion protein may also be administered to a subject in combination with the introduction of cytokines or other therapeutic reagents.

In an additional embodiment of the invention, other reagents, including derivatives reactive with the CTLA4Ig fusion protein or the CTLA4 receptor are used to regulate T cell interactions. For example, antibodies, and/or antibody fragments reactive with the CTLA4 receptor may be screened to identify those capable of inhibiting the binding of the CTLA4Ig fusion protein to the B7 antigen. The antibodies or antibody fragments such as Fab or F(ab')$_2$ fragments, may then be used to react with the T cells, for example, to inhibit T cell proliferation.

Monoclonal antibodies reactive with CTLA4 receptor, may be produced by hybridomas prepared using known procedures, such as those introduced by Kohler and Milstein (see Kohler and Milstein, Nature, 256:495–97 (1975)), and modifications thereof, to regulate cellular interactions.

These techniques involve the use of an animal which is primed to produce a particular antibody. The animal can be primed by injection of an immunogen (e.g. the B7Ig fusion protein, CTLA4Ig fusion protein or CD28Ig/CTLA4Ig hybrid fusion protein) to elicit the desired immune response, i.e. production of antibodies from the primed animal. A primed animal is also one which is expressing a disease. Lymphocytes derived from the lymph nodes, spleens or peripheral blood of primed, diseased animals can be used to search for a particular antibody. The lymphocyte chromosomes encoding desired immunoglobulins are immortalized by fusing the lymphocytes with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653, Sp2/0-Ag14, or HL1-653 myeloma lines. These myeloma lines are available from the ATCC, Rockville, Md.

The resulting cells, which include the desired hybridomas, are then grown in a selective medium such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of the desired specificity, e.g. by immunoassay techniques using the CTLA4Ig protein that has been used for immunization. Positive clones can then be subcloned under limiting dilution conditions, and the monoclonal antibody produced can be isolated.

Various conventional methods can be used for isolation and purification of the monoclonal antibodies so as to obtain them free from other proteins and contaminants. Commonly used methods for purifying monoclonal antibodies include ammonium sulfate precipitation, ion exchange chromatography, and affinity chromatography (see Zola et al., in *Monoclonal Hybridoma Antibodies: Techniques and Applications*, Hurell (ed.) pp. 51–52 (CRC Press, 1982)). Hybridomas produced according to these methods can be propagated in vitro or in vivo (in ascites fluid) using techniques known in the art (see generally Fink et al., *Prog. Clin. Pathol.*, 9:121–33 (1984), FIG. 6-1 at p. 123).

Generally, the individual cell line may be propagated in vitro, for example, in laboratory culture vessels, and the culture medium containing high concentrations of a single specific monoclonal antibody can be harvested by decantation, filtration, or centrifugation.

In addition, fragments of these antibodies containing the active binding region reactive with the extracellular domain of CTLA4 receptor, such as Fab, F(ab')$_2$ and Fv fragments may be produced. Such fragments can be produced using techniques well established in the art (see e.g. Rousseaux et al., in *Methods Enzymol.*, 121:663–69, Academic Press (1986)).

Anti-B7 monoclonal antibodies prepared as described above may be used to bind to B7 antigen to inhibit interactions of CD28-positive or CTLA4-positive T cells with B7 positive cells. Anti-CTLA4 monoclonal antibodies may be used to bind to CTLA4 receptor to inhibit the interaction of CTLA4-positive T cells with other cells.

In another embodiment, the CTLA4Ig fusion protein may be used to identify additional compounds capable of regulating the interaction between CTLA4 and the B7 antigen. Such compounds may include small naturally occurring molecules that can be used to react with B cells and/or T cells. For example, fermentation broths may be tested for the ability to inhibit CTLA4/B7 interactions. In addition, derivatives of the CTLA4Ig fusion protein as described above may be used to regulate T cell proliferation. For example, the fragments or derivatives may be used to block T cell proliferation in graft versus host (GVH) disease which accompanies allogeneic bone marrow transplantation.

The CD28-mediated T cell proliferation pathway is cyclosporine-resistant, in contrast to proliferation driven by the CD3/Ti cell receptor complex (June et al., 1987, supra). Cyclosporine is relatively ineffective as a treatment for GVH disease (Storb, *Blood* 68:119–125 (1986)). GVH disease is thought to be mediated by T lymphocytes which express CD28 antigen (Storb and Thomas, *Immunol. Rev.* 88:215–238 (1985)). Thus, the CTLA4Ig fusion protein may be useful alone, or in combination with immunosuppressants such as cyclosporine, for blocking T cell proliferation in GVH disease.

Regulation of CTLA4-positive T cell interactions with B7 positive cells, including B cells, by the methods of the invention may thus be used to treat pathological conditions such as autoimmunity, transplantation, infectious diseases and neoplasia.

The CTLA4-binding molecules and IL4-binding molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. (Quantitative Comparison of Toxicity of Anticancer Agents in Mouse, Rat, Hamster, Dog, Monkey and Man. Cancer Chemother, Rep., 50, No.4, 219–244, May 1966).

Adjustments in the dosage regimen may be made to optimize the growth inhibiting response. Doses may be divided and administered on a daily basis or the dose may be reduced proportionally depending upon the situation. For example, several divided doses may be administered daily or the dose may be proportionally reduced as indicated by the specific therapeutic situation.

In accordance with the practice of the invention an effective amount for treating a subject may be between about 0.1 and about 10 mg/kg body weight of subject. Also, the effective amount may be an amount between about 1 and about 10 mg/kg body weight of subject.

Advantages of the Invention: The subject invention overcomes the problems associated with current therapies directed to preventing the rejection of tissue or organ transplants. In contrast to present therapies, the present invention affects only immunological responses mediated by B7 interactions.

For example, the present invention affects the transplant antigen-specific T cells, thus inducing donor-specific and antigen-specific tolerance. The binding of CD28 by its ligand, B7/BB1 (B7), during T cell receptor engagement is critical for proper T cell signaling in some systems (M. K. Jenkins, P. S. Taylor, S. D. Norton, K. B. Urdahl, J. Immunol. 147:2461 (1991); C. H. June, J. A. Ledbetter, P. S. Linsley, C. B. Thompson, Immunol. Today 11:211 (1990); H. Reiser, G. J. Freeman, Z. Razi-Wolf, C. D. Gimmi, B. Benacerraf, L. M. Nadler, Proc. Natl. Acad. Sci. U.S.A. 89:271 (1992); N. K. Damle, K. Klussman, P. S. Linsley, A. Aruffo, J. Immunol. 148:1985 (1992)).

When the interaction of CD28 with its ligand is blocked, antigen-specific T cells are inappropriately induced into a state of antigen-specific T cell anergy (M. K. Jenkins, P. S. Taylor, S. D. Norton, K. B. Urdahl, J. Immunol. 147:2461 (1991); F. A. Harding, J. G. McArthur, J. A. Gross, D. H. Raulet, J. P. Allison, Nature 356:607 (1992)).

CTLA4Ig fusion protein binds to both human and murine B7 (with a 20-fold greater affinity than CD28), blocks the binding of CD28 to B7, inhibits T cell activation, and induces T cell unresponsiveness in vitro (F. A. Harding, J. G. McArthur, J. A. Gross, D. H. Raulet, J. P. Allison, Nature 356:607 (1992); P. S. Linsley et al., J. Exp. Med. 174:561 (1991).

Moreover, the present invention would be useful to obtain expression of a soluble protein product of the heretofore unexpressed CTLA4 gene, and to identify a natural ligand for CTLA4 that is involved in functional responses of T cells. The soluble protein product could then be used to regulate T cell responses in vivo to treat pathological conditions.

The following examples are presented to illustrate the present invention and to assist one of ordinary skill in making and using the same. The examples are not intended in any way to otherwise limit the scope of the invention.

EXAMPLE 1

Preparation of B7Ig and CD28Ig Fusion Proteins

Receptor-immunoglobulin C gamma (IgCγ) fusion proteins B7Ig and CD28Ig were prepared as described by Linsley et al., in *J. Exp. Med.* 173:721–730 (1991), incorporated by reference herein. Briefly, DNA encoding amino acid sequences corresponding to the respective receptor protein (e.g. B7) was joined to DNA encoding amino acid sequences corresponding to the hinge, CH2 and CH3 regions of human IgCγ1. This was accomplished as follows. Polymerase Chain Reaction (PCR).

For PCR, DNA fragments were amplified using primer pairs as described below for each fusion protein. PCR reactions (0.1 ml final volume) were run in Taq polymerase buffer (Stratagene, La Jolla, Calif.), containing 20 μmoles each of dNTP; 50–100 pmoles of the indicated primers; template (1 ng plasmid or cDNA synthesized from ≦1 μg total RNA using random hexamer primer, as described by Kawasaki in PCR Protocols, Academic Press, pp. 21–27 (1990), incorporated by reference herein); and Taq polymerase (Stratagene). Reactions were run on a thermocycler (Perkin Elmer Corp., Norwalk, Conn.) for 16–30 cycles (a typical cycle consisted of steps of 1 min at 94° C., 1–2 min at 50° C. and 1–3 min at 72° C.).

Plasmid Construction.

Expression plasmids containing cDNA encoding CD28, as described by Aruffo and Seed, *Proc. Natl. Acad. Sci. USA* 84:8573 (1987)), were provided by Drs. Aruffo and Seed (Mass General Hospital, Boston, Mass.). Plasmids containing cDNA encoding CD5, as described by Aruffo, *Cell* 61:1303 (1990)), were provided by Dr. Aruffo. Plasmids containing cDNA encoding B7, as described by Freeman et al., *J. Immunol.* 143:2714 (1989)), were provided by Dr. Freeman (Dana Farber Cancer Institute, Boston, Mass.). For initial attempts at expression of soluble forms of CD28 and B7, constructs were made (OMCD28 and OMB7) as described by Linsley et al., *J. Exp. Med.*, supra, in which stop codons were introduced upstream of the transmembrane domains and the native signal peptides were replaced with the signal peptide from oncostatin M (Malik et al., *Mol. Cell Biol.* 9:2847 (1989)). These were made using synthetic oligonucleotides for reconstruction (OMCD28) or as primers (OMB7) for PCR. OMCD28, is a CD28 cDNA modified for more efficient expression by replacing the signal peptide with the analogous region from oncostatin M. CD28Ig and B7Ig fusion constructs were made in two parts. The 5' portions were made using OMCD28 and OMB7 as templates and the oligonucleotide, CTAGCCACTGAAGCT-TCACCATGGGTGTACTGCTCACAC (SEQ ID NO:1), (encoding the amino acid sequence corresponding to the oncostatin M signal peptide) as a forward primer, and either TGGCATGGGCTCCTGATCAGGCTTA-GAAGGTCCGGGAAA (SEQ ID NO:2), or, TTTGGGCTCCTGATCAGGAAAATGCTCT-TGCTTGGTTGT (SEQ ID NO:3) as reverse primers, respectively. Products of the PCR reactions were cleaved with restriction endonucleases (Hind III and BclI) as sites introduced in the PCR primers and gel purified.

The 3' portion of the fusion constructs corresponding to human IgCγ1 sequences was made by a coupled reverse transcriptase (from Avian myeloblastosis virus; Life Sciences Associates, Bayport, N.Y.)-PCR reaction using RNA from a myeloma cell line producing human-mouse chimeric mAb L6 (provided by Dr. P. Fell and M. Gayle, Bristol-Myers Squibb Company, Pharmaceutical Research Institute, Seattle, Wash.) as template. The oligonucleotide, AAG-CAAGAGCATTTTCCTGATCAGGAGC-CCAAATCTTCTGACAAAACTCACACATC-CCCACCGTCCCCAGCACCTGAACTCCTG (SEQ ID NO:4), was used as forward primer, and CTTCGAC-CAGTCTAGAAGCATCCTCGTGCGACCGCGAGAGC (SEQ ID NO:5) as reverse primer. Reaction products were cleaved with BclI and XbaI and gel purified. Final constructs were assembled by ligating HindIII/BclI cleaved fragments containing CD28 or B7 sequences together with BclI/XbaI cleaved fragment containing IgCγ1 sequences into HindIII/XbaI cleaved CDM8. Ligation products were transformed into MC1061/p3 *E. coli* cells and colonies were screened for the appropriate plasmids. Sequences of the resulting constructs were confirmed by DNA sequencing.

The construct encoding B7 contained DNA encoding amino acids corresponding to amino acid residues from approximately position 1 to approximately position 215 of the extracellular domain of B7. The construct encoding CD28 contained DNA encoding amino acids corresponding to amino acid residues from approximately position 1 to approximately position 134 of the extracellular domain of CD28.

CD5Ig was constructed in identical fashion, using CAT-TGCACAGTCAAGCTTCCATGC-CCATGGGTTCTCTGGCCACCTTG (SEQ ID NO:6), as forward primer and ATCCACAGTGCAGTGATCATTTG-GATCCTGGCATGTGAC (SEQ ID NO:7) as reverse primer. The PCR product was restriction endonuclease digested and ligated with the IgCγ1 fragment as described above. The resulting construct (CD5Ig) encoded a mature protein having an amino acid sequence containing amino acid residues from position 1 to position 347 of the sequence corresponding to CD5, two amino acids introduced by the construction procedure (amino acids DQ), followed by DNA encoding amino acids corresponding to the IgCγ1 hinge region.

Cell Culture and Transfections.

COS (monkey kidney cells) were transfected with expression plasmids expressing CD28 and B7 using a modification of the protocol of Seed and Aruffo (*Proc. Natl. Acad. Sci.* 84:3365 (1987)), incorporated by reference herein. Cells were seeded at $10^6$ per 10 cm diameter culture dish 18–24 h before transfection. Plasmid DNA was added (approximately 15 μg/dish) in a volume of 5 mls of serum-free DMEM containing 0.1 mM chloroquine and 600 μg/ml DEAE Dextran, and cells were incubated for 3–3.5 h at 37° C. Transfected cells were then briefly treated (approximately 2 min) with 10% dimethyl sulfoxide in PBS and incubated at 37° C. for 16–24 h in DMEM containing 10% FCS. At 24 h after transfection, culture medium was removed and replaced with serum-free DMEM (6 ml/dish). Incubation was continued for 3 days at 37° C., at which time the spent medium was collected and fresh serum-free medium was added. After an additional 3 days at 37° C., the spent medium was again collected and cells were discarded.

CHO cells expressing CD28, CD5 or B7 were isolated as described by Linsley et al., (1991) supra, as follows: Briefly, stable transfectants expressing CD28, CD5, or B7, were isolated following cotransfection of dihydrofolate reductase-deficient Chinese hamster ovary (dhfr$^-$ CHO) cells with a mixture of the appropriate expression plasmid and the selectable marker, pSV2dhfr (Linsley et al., *Proc. Natl. Acad. Sci. USA* 87:5031 (1990)), incorporated by reference herein. Transfectants were then grown in increasing concentrations of methotrexate to a final level of 1 μM and were maintained in DMEM supplemented with 10% fetal bovine serum (FBS), 0.2 mM proline and 1 μM methotrexate. CHO lines expressing high levels of CD28 (CD28$^+$ CHO) or B7 (B7$^+$ CHO) were isolated by multiple rounds of fluorescence-activated cell sorting (FACS®) following indirect immunostaining with mAbs 9.3 or BB-1. Amplified CHO cells negative for surface expression of CD28 or B7 (dhfr$^+$ CHO) were also isolated by FACS® from CD28-transfected populations.

Immunostaining and FACS® Analysis.

Transfected CHO or COS cells or activated T cells were analyzed by indirect immunostaining. Before staining, CHO cells were removed from their culture vessels by incubation in PBS containing 10 mM EDTA. Cells were first incubated with murine mAbs 9.3 (Hansen et al., *Immunogenetics* 10:247 (1980)) or BB-1 (Yokochi et al., *J. Immunol.* 128:823 (1981)), or with Ig fusion proteins (all at 10 μg/ml in DMEM containing 10% FCS) for 1–2 h at 4° C. Cells were then washed, and incubated for an additional 0.5–2 h at 4° C. with a FITC-conjugated second step reagent (goat anti-mouse Ig serum for murine mAbs, or goat anti-human Ig Cγ serum for fusion proteins (Tago, Inc., Burlingame, Calif.)). Fluorescence was analyzed on a FACS IV® cell sorter (Becton Dickinson and CO., Mountain View, Calif.) equipped with a four decade logarithmic amplifier.

Purification of Ig Fusion Proteins.

The first, second and third collections of spent serum-free culture media from transfected COS cells were used as sources for the purification of Ig fusion proteins. After removal of cellular debris by low speed centrifugation, medium was applied to a column (approximately 200–400 ml medium/ml packed bed volume) of immobilized protein A (Repligen Corp., Cambridge, Mass.) equilibrated with 0.05M sodium citrate, pH 8.0. After application of the medium, the column was washed with 1M potassium phosphate, pH 8, and bound protein was eluted with 0.05M sodium citrate, pH 3. Fractions were collected and immediately neutralized by addition of $\frac{1}{10}$ volume of 2M Tris, pH 8. Fractions containing the peak of $A_{280}$ absorbing material were pooled and dialyzed against PBS before use. Extinction coefficients of 2.4 and 2.8 ml/mg for CD28Ig and B7Ig, respectively, were determined by amino acid analysis of solutions of known absorbance. The recovery of purified CD28Ig and B7Ig binding activities was nearly quantitative as judged by FACS® analysis after indirect fluorescent staining of B7$^+$ and CD28$^+$ CHO cells.

EXAMPLE 2

Preparation of CTLA4Ig Fusion Protein

A soluble genetic fusion encoding CTLA4Ig between the extracellular domain of CTLA4 and an IgCγ1 domain was constructed in a manner similar to that described above for the CD28Ig construct. The extracellular domain of the CTLA4 gene was cloned by PCR using synthetic oligonucleotides corresponding to the published sequence (Dariavach et al., *Eur. Journ. Immunol.* 18:1901–1905 (1988)).

Because a signal peptide for CTLA4 was not identified in the CTLA4 gene, the N-terminus of the predicted sequence of CTLA4 was fused to the signal peptide of oncostatin M (Malik et al., *Mol. and Cell. Biol.* 9:2847 (1989)) in two steps using overlapping oligonucleotides. For the first step, the oligonucleotide, CTCAGTCTGGTCCTTGCACTCCT-GTTTCCAAGCATGGCGAGCATGGCAATG-CACGTGGCCCAGCC (SEQ ID NO:8) (which encoded the C terminal 15 amino acids from the oncostatin M signal peptide fused to the N terminal 7 amino acids of CTLA4) was used as forward primer, and TTTGGGCTCCTGATCA-GAATCTGGGCACGGTTG (SEQ ID NO:9) (encoding amino acid residues 119–125 of the amino acid sequence encoding CTLA4 receptor and containing a Bcl I restriction enzyme site) as reverse primer. The template for this step was cDNA synthesized from 1 μg of total RNA from H38 cells (an HTLV II infected T cell leukemic cell line provided by Drs. Salahudin and Gallo, NCI, Bethesda, Md.). A portion of the PCR product from the first step was reamplified, using an overlapping forward primer, encoding the N terminal portion of the oncostatin M signal peptide and containing a Hind III restriction endonuclease site, CTAGC-CACTGAAGCTTCACCAATGGGTGTACT-GCTCACACAGAGGACGCTGCTCAGTCTG-GTCCTTGCACTC (SEQ ID NO:10) and the same reverse primer. The product of the PCR reaction was digested with Hind III and Bcl I and ligated together with a Bcl 1/Xba I cleaved cDNA fragment encoding the amino acid sequences corresponding to the hinge, CH2 and CH3 regions of IgCγ1 into the Hind III/Xba I cleaved expression vector, CDM8 or Hind III/Xba I cleaved expression vector πLN (provided by Dr. Aruffo).

A map of the resulting CTLA4Ig fusion construct is shown in FIG. 1. Sequences displayed in this figure show the junctions between CTLA4 (upper case letters, unshaded regions) and the signal peptide, SP, of oncostatin M (dark shaded regions), and the hinge, H, of IgCγ1 (stippled regions). The amino acid in parentheses was introduced during construction. Asterisks (*) indicate cysteine to serine mutations introduced in the IgCγ hinge region. The immunoglobulin superfamily V-like domain present in CTLA4 is indicated, as are the CH2 and CH3 domains of IgCγ1.

Expression plasmids, CDM8, containing CTLA4Ig were then transfected into COS cells using DEAE/dextran transfection by modification (Linsley et al., 1991, supra) of the protocol described by Seed and Aruffo, 1987, supra.

Expression plasmid constructs (πLN or CDM8) containing cDNA encoding the amino acid sequence of CTLA4Ig, was transfected by lipofection using standard procedures into dhfr− CHO lines to obtain novel cell lines stably expressing CTLA4Ig.

DNA encoding the amino acid sequence corresponding to CTLA4Ig has been deposited with the ATCC under the Budapest Treaty on May 31, 1991, and has been accorded ATCC accession number 68629.

A preferred stable transfectant, expressing CTLA4Ig, designated Chinese Hamster Ovary Cell Line, CTLA4Ig-24, was made by screening B7 positive CHO cell lines for B7 binding activity in the medium using immunostaining. Transfectants were maintained in DMEM supplemented with 10% fetal bovine serum (FBS), 0.2 mM proline and 1 µM methotrexate.

The CTLA4Ig-24 CHO cell line has been deposited with the ATCC under the Budapest Treaty on May 31, 1991 and has been accorded accession number ATCC 10762.

Figure 2:
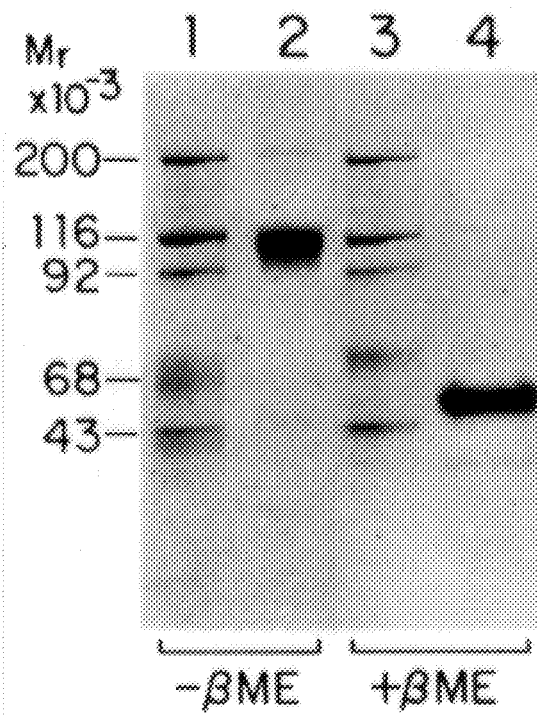
FIG. 2 is a photograph of a gel obtained from SDS-PAGE chromatographic purification of CTLA4Ig as described in Example 2, infra.

CTLA4Ig was purified by protein A chromatography from serum-free conditioned supernatants (FIG. 2). Concentrations of CTLA4Ig were determined assuming an extinction coefficient at 280 nm of 1.6 (experimentally determined by amino acid analysis of a solution of known absorbance). Molecular weight standards (lanes 1 and 3, FIG. 2) and samples (1 µg) of CTLA4Ig (lanes 2 and 4) were subjected to SDS-PAGE (4–12% acrylamide gradient) under non-reducing conditions (−βME, lanes 1 and 2) or reducing conditions (+βME, lanes 3 and 4) Proteins were visualized by staining with Coomassie Brilliant Blue.

Under non-reducing conditions, CTLA4Ig migrated as a $M_r$ approximately 100,000 species, and under reducing conditions, as a $M_r$ approximately 50,000 species (FIG. 2). Because the IgC γ hinge disulfides were eliminated during construction, CTLA4Ig, like CD28Ig, is a dimer presumably joined through a native disulfide linkage.

EXAMPLE 3
CTLA4 Receptor

To reconstruct DNA encoding the amino acid sequence corresponding to the full length human CTLA4 gene, cDNA encoding amino acids corresponding to a fragment of the transmembrane and cytoplasmic domains of CTLA4 was cloned by PCR and then joined with cDNA encoding amino acids corresponding to a fragment from CTLA4Ig that corresponded to the oncostatin M signal peptide fused to the N-terminus of CTLA4. Procedures for PCR, and cell culture and transfections were as described above in Example 1 using COS cells and DEAE-dextran transfection.

Because the expression of CTLA4 receptor protein in human lymphoid cells has not been previously reported, it was necessary to locate a source of CTLA4 mRNA. PCR cDNA reverse transcribed from the total cellular RNA of H38 cells, as noted above, was used for cloning by PCR. For this purpose, the oligonucleotide, GCAATGCACGTGGC-CCAGCCTGCTGTGGTAGTG (SEQ ID NO:11), (encoding the first 11 amino acids in the predicted coding sequence) was used as a forward primer, and TGATGTAA-CATGTCTAGATCAATTGATGG-GAATAAAATAAGGCTG (SEQ ID NO:12) (homologous to the last 8 amino acids in CTLA4 and containing a Xba I site) as reverse primer. The template again was a cDNA synthesized from 1 µg RNA from H38 cells. Products of the PCR reaction were cleaved with the restriction endonucleases Nco I and Xba I and the resulting 316 bp product was gel purified. A 340 bp Hind III/Nco I fragment from the CTLAIg fusion described above was also gel-purified, and both restriction fragments were ligated into Hind III/Xba I cleaved CDM8 to form OMCTLA.

The resulting construct corresponded to full length CTLA4 (SEQ ID NOs: 13 and 14) and the oncostatin M signal peptide. The construct is shown in FIG. 3 and was designated OMCTLA4. The sequence for CTLA4 shown in FIG. 3 differs from the predicted human CTLA4 DNA sequence (Dariavach et al., supra) by a base change such that the previously reported alanine at amino acid position 111 of the amino acid sequence shown, encodes a threonine. This threonine is part of a newly identified N-linked glycosylation site that may be important for successful expression of the fusion protein.

Ligation products were transformed into MC1061/p3 E. coli cells and colonies were screened for the appropriate plasmids. Sequences of the resulting constructs were confirmed by DNA sequence analysis.

EXAMPLE 4
Characterization of CTLA4Ig

To characterize the CTLA4Ig constructs, several isolates, CD28Ig, B7Ig, and CD5Ig, were prepared as described above and were transfected into COS cells as described in Examples 2 and 3, and were tested by FACS® analysis for binding of B7Ig. In addition to the above-mentioned constructs, CDM8 plasmids containing cDNAs encoding CD7 as described by Aruffo and Seed, (EMBO Jour. 6:3313–3316 (1987)), incorporated by reference herein, were also used.

mAbs. Murine monoclonal antibodies (mAbs) 9.3 (anti-CD28) and G19-4 (anti-CD3), G3-7 (anti-CD7), BB-1 (anti-B7 antigen) and rat mAb 187.1 (anti-mouse K chain) have been described previously (Ledbetter et al., Proc. Natl. Acad. Sci. 84:1384–1388 (1987); Ledbetter et al., Blood 75:1531 (1990); Yokochi et al., supra) and were purified from ascites before use. The hybridoma producing mAb OKT8 was obtained from the ATCC, Rockville, Md., and the mAb was also purified from ascites before use. mAb 4G9 (anti-CD19) was provided by Dr. E. Engleman, Stanford University, Palo Alto, Calif.). Purified human-mouse chimeric mAb L6 (having human Cγ1 Fc portion) was a gift of Dr. P. Fell and M. Gayle (Bristol-Myers Squibb Pharmaceutical Research Institute, Seattle, Wash.).

Immunostaining and FACS® Analysis.

Prior to staining, COS or CHO cells were removed from their culture vessels by incubation in PBS containing 10 mM EDTA. Cells were first incubated with mAbs or Ig fusion proteins at 10 µg/ml in DMEM containing 10% FBS for 1–2 hr at 4° C. Cells were then washed, and incubated for an additional 0.5–2 hrs at 4° C. with FITC-conjugated goat anti-mouse immunoglobulin or with FITC-conjugated goat anti-human Ig C γ serum (both from Tago, Burlingame, Calif.). When binding of both mAbs and Ig fusion proteins were measured in the same experiment, FITC-conjugated anti-mouse and anti-human second step reagents were mixed together before use. Fluorescence on a total of 10,000 cells was then analyzed by FACS®.

Peripheral Blood Lymphocyte Separation and Stimulation.

Peripheral blood lymphocytes (PBLs) were isolated by centrifugation through Lymphocyte Separation Medium (Litton Bionetics, Kensington, Md.). Alloreactive T cells were isolated by stimulation of PBL in a primary mixed lymphocyte reaction (MLR). PBL were cultured at $10^6$/ml irradiated (5000 rad) T51 LCL. EBV-transformed lymphoblastoid cell lines (LCL), PM (Bristol-Myers Squibb Co.) and T51 (Bristol-Myers Squibb Co.) were maintained in RPMI supplemented with 10% FBS. After 6 days, alloreactive "blasts" cells were cryopreserved. Secondary MLR were conducted by culturing thawed alloreactive blasts together with fresh irradiated T51 LCL in the presence and absence of mAbs and Ig fusion proteins. Cells were cultured in 96 well flat bottom plates ($4\times10^4$ alloreactive blasts and $1\times10^4$ irradiated T51 LCL cells/well, in a volume of 0.2 ml) in RPMI containing 10% FBS. Cellular proliferation of quadruplicate cultures was measured by uptake of [$^3$H]-thymidine during the last 6 hours of a 2–3 day culture.

PHA-activated T cells were prepared by culturing PBLs with 1 μg/ml PHA (Wellcome, Charlotte, N.C.) for five days, and one day in medium lacking PHA. Viable cells were collected by sedimentation through Lymphocyte Separation Medium before use. Cells were stimulated with mAbs or transfected CHO cells for 4–6 hr at 37° C., collected by centrifugation and used to prepare RNA.

CD4$^+$ T cells were isolated from PBLs by separating PBLs from healthy donors into T and non-T cells using sheep erythrocyte rosetting technique and further separating T cells by panning into CD4$^+$ cells as described by Damle et al., *J. Immunol.* 139:1501 (1987), incorporated by reference herein. B cells were also purified from peripheral blood by panning as described by Wysocki and Sato, *Proc. Natl. Acad. Sci.* 75:2844 (1978), incorporated by reference herein, using anti-CD19 mAb 4G9. To measure $T_h$-induced Ig production, $10^6$ CD4$^+$ T cells were mixed with $10^6$ CD19$^+$ B cells in 1 ml of RPMI containing 10% FBS. Following culture for 6 days at 37° C., production of human IgM was measured in the culture supernatants using solid phase ELISA as described by Volkman et al., *Proc. Natl. Acad. Sci. USA* 78:2528 (1981), incorporated by reference herein. Briefly, 96-well flat bottom microtiter ELISA plates (Corning, Corning, N.Y.) were coated with 200 μl/well of sodium carbonate buffer (pH 9.6) containing 10 μg/ml of affinity-purified goat anti-human IgG or IgM antibody (Tago, Burlingame, Calif.), incubated overnight at 4° C., and then washed with PBS and wells were further blocked with 2% BSA in PBS (BSA-PBS). Samples to be assayed were added at appropriate dilution to these wells and incubated with 200 μl/well of 1:1000 dilution of horseradish peroxidase (HRP)-conjugated F(ab')$_2$ fraction of affinity-purified goat anti-human IgG or IgM antibody (Tago). The plates were then washed, and 100 μl/well of o-phenylenediamine (Sigma Chemical Co., St. Louis, Mo.) solution (0.6 mg/ml in citrate-phosphate buffer with pH 5.5 and 0.045% hydrogen peroxide). Color development was stopped with 2N sulfuric acid. Absorbance at 490 nm was measured with an automated ELISA plate reader. Test and control samples were run in triplicate and the values of absorbance were compared to those obtained with known IgG or IgM standards run simultaneously with the supernatant samples to generate the standard curve using which the concentrations of Ig in the culture supernatant were quantitated. Data are expressed as ng/ml of Ig±SEM of either triplicate or quadruplicate cultures.

Immunoprecipitation Analysis and SDS PAGE.

Cells were surface-labeled with $^{125}$I and subjected to immunoprecipitation analysis. Briefly, PHA-activated T cells were surface-labeled with $^{125}$I using lactoperoxidase and H$_2$O$_2$ as described by Vitetta et al., *J. Exp. Med.* 134:242 (1971), incorporated by reference herein. SDS-PAGE chromatography was performed on linear acrylamide gradients gels with stacking gels of 5% acrylamide. Gels were stained with Coomassie Blue, destained, and photographed or dried and exposed to X ray film (Kodak XAR-5).

Binding Assays.

B7Ig was labeled with $^{125}$I to a specific activity of approximately $2\times10^6$ cpm/pmole. Ninety-six well plastic dishes were coated for 16–24 hrs with a solution containing CTLA4Ig (0.5 μg in a volume of 0.05 ml of 10 mM Tris, pH 8). Wells were blocked with binding buffer (DMEM containing 50 mM BES (Sigma Chemical Co.), pH 6.8, 0.1% BAS, and 10% FCS) before addition of a solution (0.09 ml) containing $^{125}$I B7Ig (approximately $5\times10^5$ cpm) in the presence or absence of competitor. Following incubation for 2–3 hrs at 23° C., wells were washed once with binding buffer, and four times with PBS. Bound radioactivity was then solubilized by addition of 0.5N NaOH, and quantified by gamma counting.

Binding to B7Ig.

Figure 4:
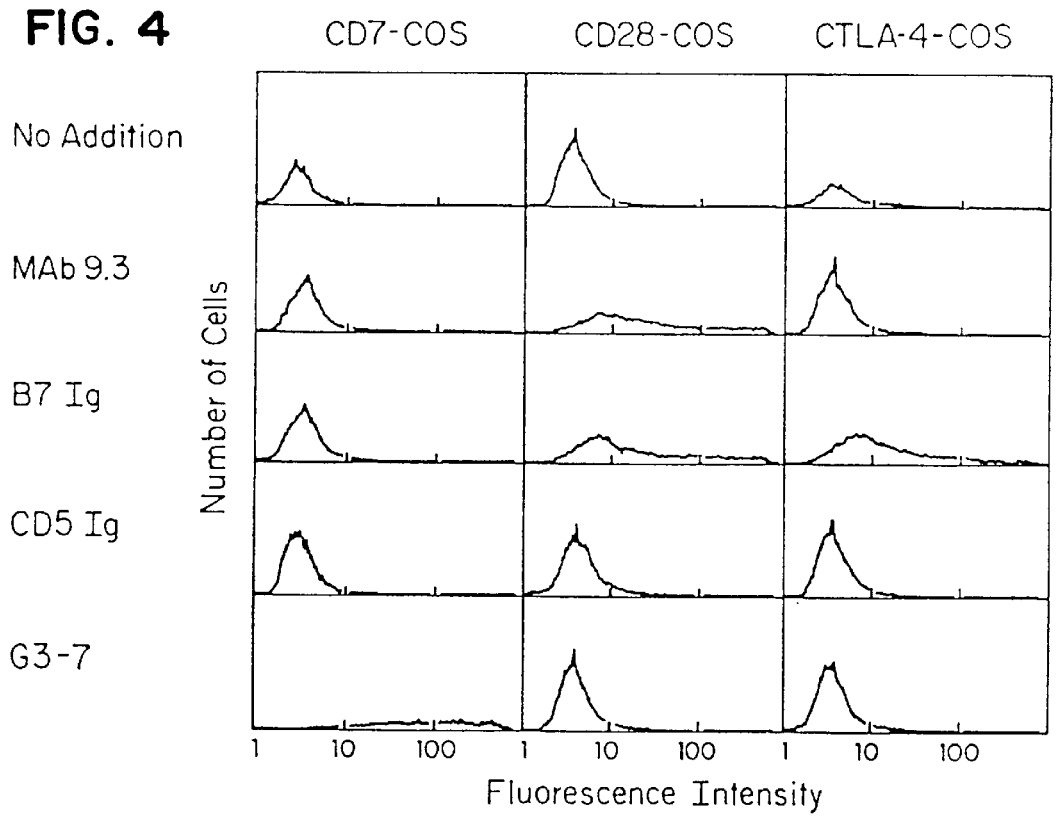
FIG. 4 depicts the results of FACS® analysis of binding of the B7Ig fusion protein to CD28- and CTLA4-transfected COS cells as described in Example 4, infra.

The functional activity of the OMCTLA4 construct encoding the complete human CTLA4 DNA gene, is shown in the experiment shown in FIG. 4. COS cells were transfected with expression plasmids CD7, OMCD28 and OMCTLA4 as described above. Forty-eight hours following transfection, cells were collected and incubated with medium only (no addition) or with mAbs 9.3, B7Ig, CD5Ig or G3-7. Cells were then washed and binding was detected by a mixture of FITC-conjugated goat anti-mouse Ig and FITC-conjugated goat anti-human Ig second step reagents. Transfected cells were tested for expression of the appropriate cell surface markers by indirect immunostaining and fluorescence was measured using FACS® analysis as described above.

As shown in FIG. 4, mAb 9.3 bound to CD28-transfected COS cells, but not to CTLA4-transfected cells. In contrast, the B7Ig fusion protein (but not control CD5Ig fusion protein) bound to both CD28- and CTLA4-transfected cells. CD7-transfected COS cells bound neither mAb 9.3 nor either of the fusion proteins. This indicates that CD28 and CTLA4 both bind the B cell activation antigen, B7. Furthermore, mAb 9.3 did not detectably bind CTLA4.

Binding of CTLA4Ig on B7 Positive CHO cells.

Figure 5:
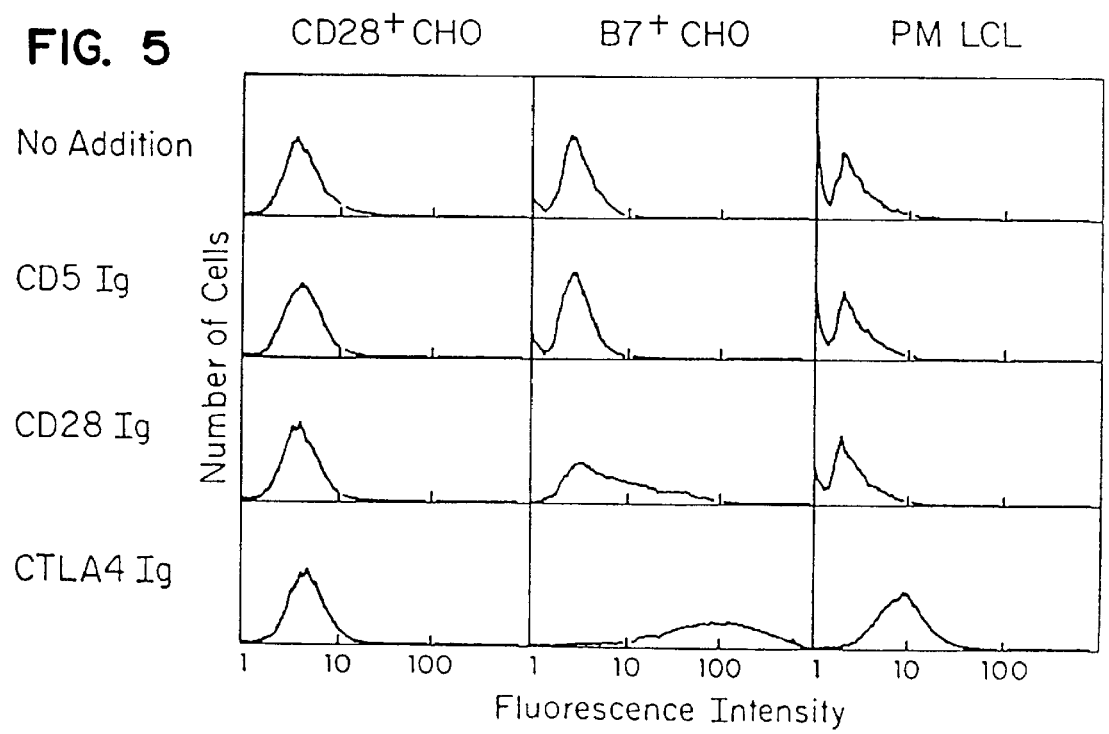
FIG. 5 depicts the results of FACS® analysis of binding of purified CTLA4Ig on B7 antigen-positive (B7$^+$) CHO cells and on a lymphoblastoid cell line (PM LCL) as described in Example 4, infra.

To further characterize the binding of CTLA4Ig and B7, the binding activity of purified CTLA4Ig on B7$^+$ CHO cells and on a lymphoblastoid cell line (PM LCL) was measured in the experiment shown in FIG. 5. Amplified transfected CHO cell lines and PM LCLs were incubated with medium only (no addition) or an equivalent concentration of human IgCγ1-containing proteins (10 μg/ml) of CD5Ig, CD28Ig or CTLA4Ig. Binding was detected by FACS® following addition of FITC-conjugated goat anti-human Ig second step reagents. A total of 10,000 stained cells were analyzed by FACS®.

As shown in FIG. 5, CD28Ig bound to B7$^+$ CHO cells but not to PM LCL, a cell line which expresses relatively low levels of the B7 antigen (Linsley et al., supra, 1990). CTLA4Ig bound more strongly to both cell lines than did CD28Ig, suggesting that it bound with higher affinity. Neither CD28Ig nor CTLA4Ig bound to CD28$^+$ CHO cells.

Affinity of Binding of CTLA4Ig and B7Ig.

The apparent affinity of interaction between CTLA4Ig and B7Ig was then measured using a solid phase competition binding assay. Ninety-six well plastic dishes were coated with CTLA4Ig as described above. B7Ig was radiolabeled with $^{125}$I ($5\times10^5$ cpm, $2\times10^6$ cpm/pmole), and added to a concentration of 4 nM in the presence of the indicated concentrations (see FIG. 6) of unlabeled chimeric mAb L6, mAb 9.3, mAb BB-1 or B7Ig. Plate-bound radioactivity was determined and expressed as a percentage of radioactivity bound to wells treated without competitor (28,300 cpm). Each point represents the mean of duplicate determinations; replicates generally varied from the mean by ≤20%. Concentrations were calculated based on a $M_r$ of 75,000 per binding site for mAbs and 51,000 per binding site for B7Ig.

Figure 6:
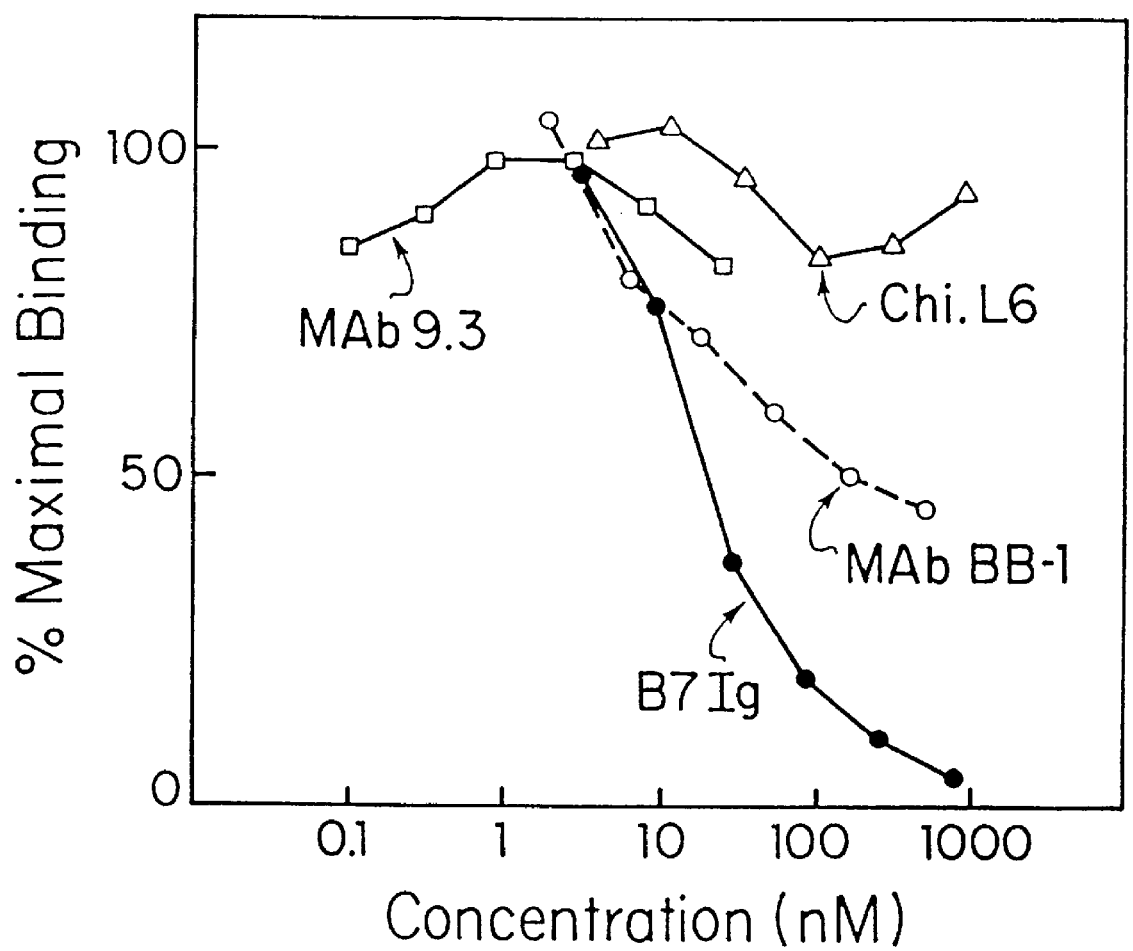
FIG. 6 is a graph illustrating competition binding analysis of $^{125}$I labeled B7Ig to immobilized CTLA4Ig as described in Example 4, infra.

As shown in FIG. 6, only mAb BB-1 and unlabeled B7Ig competed significantly for $^{125}$I-B7Ig binding (half maximal effects at approximately 22 nM and approximately 175 nM, respectively). Neither chimeric mAb L6, nor mAb 9.3 competed effectively at the concentrations tested. In other experiments, the concentrations of mAb 9.3 used were sufficient to inhibit binding of $^{125}$I-B7Ig to immobilized CD28Ig or to cell surface expressed CD28 by ≧90%.

Figure 7:
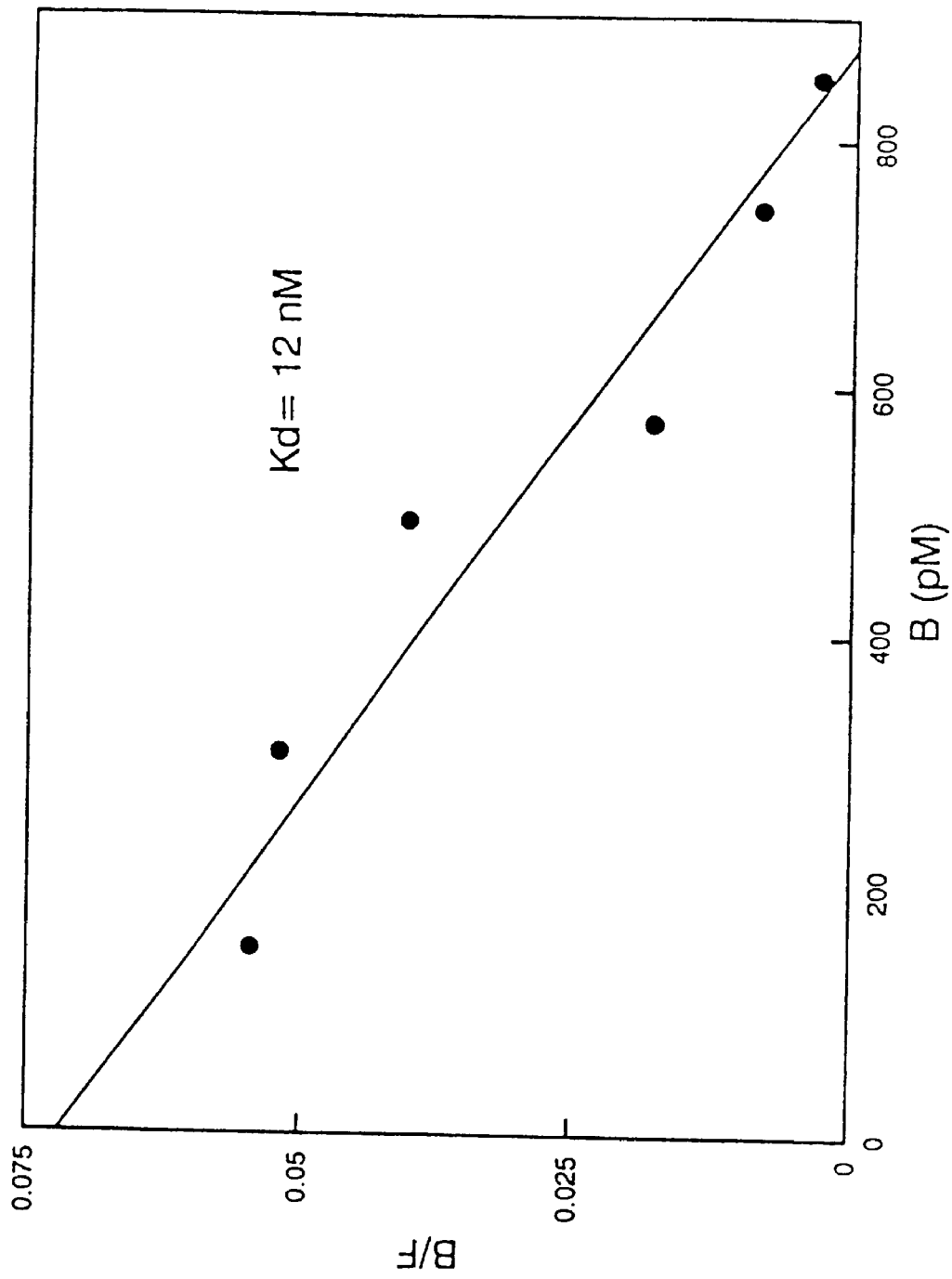
FIG. 7 is a graph showing the results of Scatchard analysis of $^{125}$I-labeled B7Ig binding to immobilized CTLA4Ig as described in Example 4, infra.

When the competition data from FIG. 6 were plotted in a Scatchard representation, a dissociation constant, $K_d$, of approximately 12 nM was calculated for binding of $^{125}$I-B7 to immobilized CTLA4Ig (FIG. 7). This value is approximately 20 fold lower than the previously determined $K_d$ of binding between $^{125}$I-B7Ig and CD28 (approximately 200 nM) (Linsley et al, (1991), supra) indicating that CTLA4 is a higher affinity receptor for the B7 antigen than CD28 receptor.

Figure 8:
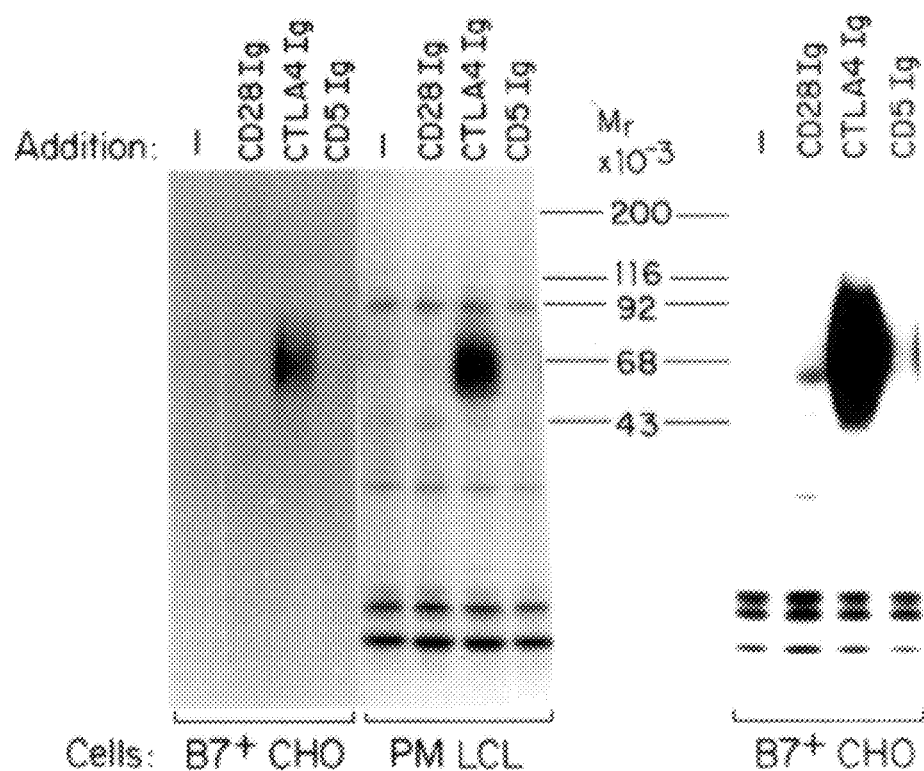
FIG. 8 is a photograph of a gel from SDS-PAGE chromatography of immunoprecipitation analysis of B7 positive CHO cells and PM LCL cells surface-labeled with $^{125}$I as described in Example 4, infra.

To identify the molecule(s) on lymphoblastoid cells which bound CTLA4Ig (FIG. 7), $^{125}$I-surface labeled cells were subjected to immunoprecipitation analysis (FIG. 8). B7$^+$ CHO and PM LCL cells were surface-labeled with $^{125}$I, and extracted with a non-ionic detergent solution as described above. Aliquots of extracts containing approximately 1.5× 10$^7$ cpm in a volume of 0.1 ml were subjected to immunoprecipitation analysis as described above with no addition, or 2 μg each of CD28Ig, CTLA4Ig or CD5Ig. Washed immunoprecipitates were then analyzed by SDS-PAGE (10–20% acrylamide gradient) under reducing conditions. The gel was then dried and subjected to autoradiography. The left panel of FIG. 8 shows an autoradiogram obtained after a 1 day exposure. The right panel of FIG. 8 shows an autoradiogram of the same gel after a 10 day exposure. The autoradiogram in the center panel of FIG. 8 was also exposed for 10 days. Positions of molecular weight standard are also indicated in this figure.

As shown by FIG. 8, a diffusely migrating ($M_r$ approximately 50,000–75,000; center at approximately 60,000) radiolabeled protein was immunoprecipitated by CTLA4Ig, but not by CD28Ig or CD5Ig. This molecule co-migrated with B7 immunoprecipitated from B7$^+$ CHO cells by CTLA4Ig, and much more weakly, by CD28Ig. These findings indicate that CTLA4Ig binds a single protein on lymphoblastoid cells which is similar in size to the B7 antigen.

Inhibition of Immune Responses In Vitro by CTLA4Ig

Inhibition of Proliferation. Previous studies have shown that the anti-CD28 mAb, mAb 9.3, and the anti-B7 mAb, mAb BB-1, inhibit proliferation of alloantigen specific $T_h$ cells, as well as immunoglobulin secretion by alloantigen-presenting B Cells (Damle, et al., *Proc. Natl. Acad. Sci.* 78:5096 (1981); Lesslauer et al., *Eur. J. Immunol.* 16:1289 (1986)). Because CTLA4 is a high affinity receptor for the B7 antigen as demonstrated herein, soluble CTLA4Ig was tested for its ability to inhibit these responses. The effects of CTLA4Ig on T cell proliferation were examined in the experiment shown in FIG. 9.

Figure 9:
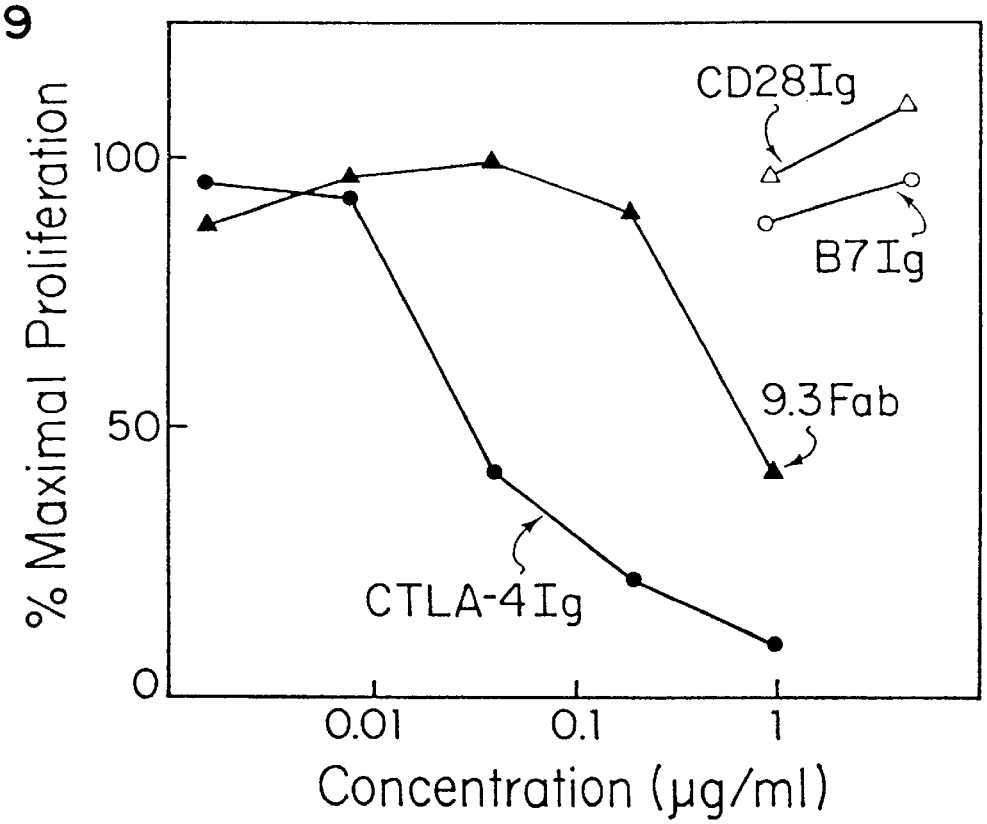
FIG. 9 is a graph depicting the effects on proliferation of T cells of CTLA4Ig as measured by [$^3$H]-thymidine incorporation as described in Example 4, infra.

Primary mixed lymphocyte reaction (MLR) blasts were stimulated with irradiated T51 lymphoblastoid cells (LC) in the absence or presence of concentrations of murine mAb 9.3 Fab fragments, or B7Ig, CD28Ig or CTLA4Ig immunoglobulin Cγ fusion proteins. Cellular proliferation was measured by [$^3$H]-thymidine incorporation after 4 days and is expressed as the percentage of incorporation by untreated cultures (21,000 cpm). FIG. 9 shows the means of quadruplicate determinations (SEM ≦10%).

As shown in FIG. 9, CTLA4Ig inhibited the MLR reaction in a dose-dependant fashion by a maximum of >90% with a ½ maximal response at approximately 30 ng/ml (approximately 0.8 nM). The Fab fragment of mAb 9.3, which previously was shown to be a more potent inhibitor of MLR than whole mAb 9.3 (Damle et al., *J. Immunol.* 140:1753–1761 (1988)), also inhibited the MLR, but at higher concentrations (approximately 800 ng/ml or approximately 30 nM for ½ maximal response). B7Ig and CD28Ig did not significantly inhibit the MLR even at higher concentrations. In another experiment, addition of B7Ig together with CTLA4Ig partially overcame the inhibition of MLR by CTLA4Ig, indicating that the inhibition was specifically due to interactions with B7 antigen.

Inhibition of Immunoglobulin Secretion.

Figure 10:
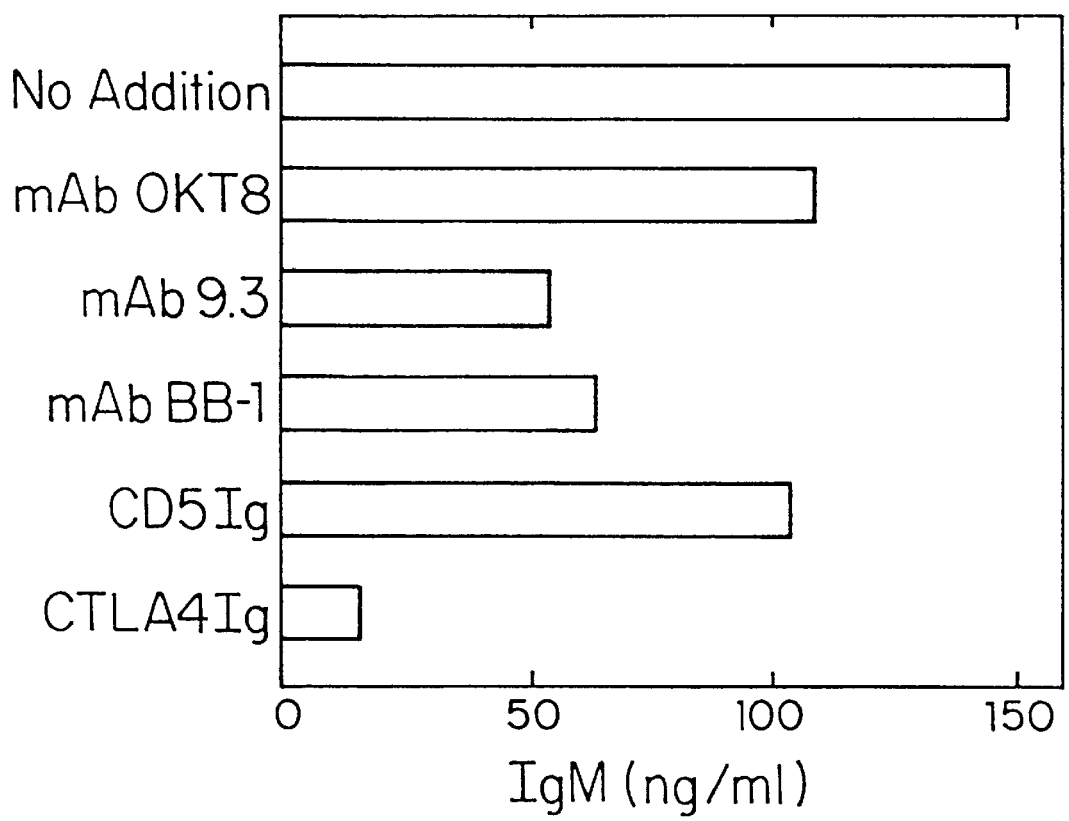
FIG. 10 is a bar graph illustrating the effects of CTLA4Ig on helper T cell ($T_h$)-induced immunoglobulin secretion by human B cells as determined by enzyme immunoassay (ELISA) as described in Example 4, infra.

The effects of CTLA4Ig on helper T cell ($T_h$)-induced immunoglobulin secretion were also examined (FIG. 10). CD4$^+$ T cells were mixed with allogeneic CD19$^+$ B cells in the presence or absence of the indicated immunoglobulin molecules as described above. Murine mAbs OKT8, 9.3 and BB-1 were added at 20 μg/ml, and Ig fusion proteins at 10 μg/ml. After 6 days of culture, concentrations of human IgM (SEM <5%) in culture supernatants were determined by enzyme immunoassay (ELISA) as described above. IgM production by B cells cultured in the absence of CD4$^+$ T cells was 11 ng/ml.

As shown in FIG. 10, CD4$^+$ T cells stimulated IgM production by allogenic CD19$^+$ B Cells (in the absence of CD4$^+$ T cells, IgM levels were reduced by 93%). mAbs 9.3 and BB-1 significantly inhibited $T_h$-induced IgM production (63% and 65% inhibition, respectively). CTLA4Ig was even more effective as an inhibitor (89% inhibition) than were these mAbs. Inhibition by control Ig molecules, mAb OKT8 and CD5Ig, was much less (≦30% inhibition). None of these molecules significantly inhibited Ig production measured in the presence of *Staphylococcal aureus* enterotoxin B. Similar results were obtained with CD4$^+$ T cells and B cells derived from other donors. These results indicate that the inhibition by CTLA4Ig is specific.

The above data also demonstrate that the CTLA4 and CD28 receptors are functionally as well as structurally related. Like CD28, CTLA4 is also a receptor for the B cell activation antigen, B7. CTLA4Ig bound $^{125}$I-B7 with an affinity constant, $K_d$, of approximately 12 nM, a value some 20 fold higher than the affinity between CD28 and B7Ig (approximately 200 nM). Thus, CTLA4 and CD28 may be thought of as high and low affinity receptors, respectively, for the same ligand, the B7 antigen.

The apparent affinity between CD28 and B7 is similar to the affinity reported for binding of soluble alloantigen to the T cell receptor of a murine T cell hybridoma (approximately 100 nM; Schnek et al., *Cell* 56:47 (1989)), and is higher affinity than interactions between CD2 and LFA3 (Recny et al., *J. Biol. Chem.* 265:8542 (1990)), or CD4 and MHC class II molecules (Clayton et al., *Nature* 339:548 (1989)). The apparent affinity constant, $K_d$, between CTLA4 and B7 is even greater, and compares favorably with higher affinity mAbs ($K_d$ 2–10,000 nM; Alzari et al., *Ann. Rev. Immuno.* 6:555 (1988)). The $K_d$ between CTLA4 and B7 is similar to or greater than $K_d$ values of integrin receptors and their ligands (10–2000 nM; Hautanen et al., *J. Biol. Chem.* 264:1437–1442 (1989); Di Minno et al., *Blood* 61:140–148 (1983); Thiagarajan and Kelley, *J. Biol. Chem.* 263:035–3038 (1988)). The affinity of interaction between CTLA4 and B7 is thus among the highest yet reported for lymphoid adhesion systems.

These results demonstrate the first expression of a functional protein product of CTLA4 transcripts. CTLA4Ig, a fusion construct containing the extracellular domain of CTLA4 fused to an IgCγ1 domain, forms a disulfide-linked dimer of $M_r$ approximately 50,000 subunits (FIG. 1).

Because no interchain disulfides would be predicted to form in the Ig portion of this fusion, it seems likely that cysteines from CTLA4 are involved in disulfide bond formation. The analogous CD28Ig fusion protein (Linsley et al, supra, 1991) also contains interchain disulfide linkage(s). These results suggest that CTLA4 receptor, like CD28 (Hansen et al., *Immunogenetics* 10:247–260 (1980)), exists on the T cell surface as a disulfide linked homodimer. Although CD28 and CTLA4 are highly homologous proteins, they are immunologically distinct, because the anti-CD28 mAb, mAb 9.3, does not recognize CTLA4 (FIGS. 4 and 5).

It is not known whether CTLA4 can activate T cells by a signalling pathway analogous to CD28. The cytoplasmic domains of murine and human CTLA4 are identical (Dariavach et al., supra 1988), suggesting that this region has important functional properties. The cytoplasmic domains of CD28 and CTLA4 also share homology, although it is unclear if this is sufficient to impart similar signaling properties to the two molecules.

CTLA4Ig is a potent inhibitor of in vitro lymphocyte functions requiring T cell and B cell collaboration (FIGS. 9 and 10). These findings, together with previous studies, indicate the fundamental importance of interactions between B7 antigen and its counter-receptors, CD28 and/or CTLA4, in regulating both T and B lymphocyte responses. CTLA4Ig should be a useful reagent for future investigations on the role of these interactions during immune responses. CTLA4Ig is a more potent inhibitor of in vitro lymphocyte responses than either mAb BB-1 or mAb 9.3 (FIGS. 9 and 10). The greater potency of CTLA4Ig over mAb BB-1 is most likely due to the difference in affinities for B7 between these molecules (FIG. 6). CTLA4Ig is also more potent than mAb 9.3, probably because, unlike the mAb, it does not also have direct stipulatory effects on T cell proliferation (June et al., *Immunology Today* 11:211 (1989)) to counteract its inhibitory effects. The immunosuppressive effects of CTLA4Ig in vitro suggest that future investigations are warranted into possible therapeutic effects of this molecule for treatment of autoimmune disorders involving aberrant T cell activation or Ig production.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

EXAMPLE 5

Female BALB/c (H-$2^d$) and C57BL/6 (H-$2^d$)mice, 6 to 8 wk. of age were obtained from The Jackson Laboratory (Bar Harbor, Me.).

Human pancreatic islets cells were purified after collagenase digestion as described (C. Ricordi et al. Transplantation 52:519 (1991); A. G. Tzakis et al. Lancet 336:402 (1990); C. Ricordi, P. E. Lacy, E. H. Finke, B. J. Olack, D. W. Scharp, Diabetes 37:413 (1988)).

B6 or B10 mice, treated with streptozocin (175 mg per kilogram of body weight) 3 to 5 days before transplant and exhibiting nonfasting plasma glucose levels of greater than 280 mg/dl (with the majority over 300 mg/ml), were used as recipients.

Each animal received approximately 800 fresh human islets of 150 μm in diameter beneath the left renal capsule (D. Faustman and C. Coe, Science 252:1700 (1991); Y. J. Zeng et al. Transplantation 53:277 (1992)). Treatment was started immediately after transplantation.

Control animals were treated with PBS (solid lines) or L6 (dotted lines) at 50 μg every other day for 14 days immediately after transplantation (FIG. 11A). Islet transplants were considered rejected when glucose levels were greater than 250 mg/dl for three consecutive days. Animals treated with PBS (n=14) and L6 (n=8) had mean graft survivals of 5.6 and 6.4 days, respectively.

Animals were treated with 10 μg of CTLA4Ig for 14 consecutive days immediately after transplant (n=7) (FIG. 11B). Three out of seven animals maintained their grafts for >80 days. The remaining four animals had a mean graft survival of 12.75 days.

Animals were treated with 50 μg of CTLA4Ig every other day for 14 days immediately after human islet transplantation (FIG. 11C). All animals (n=12) treated with this dose maintained grafts throughout the analysis (FIG. 11C). Selected mice were nephrectomized on days 21 and 29 after the transplant to assess the graft's function (FIG. 11C).

Histology was performed on kidneys transplanted with human islet cells (FIGS. 12A, 12B, 12C, 12D). The slides were analyzed blindly.

Figure 12A:
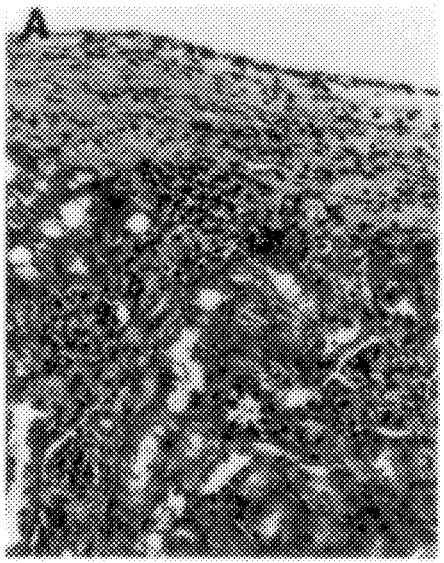
FIGS. 12A, 12B, 12C, and 12D are photographs of histopathology slides of human islets transplanted under the kidney capsule of B10 mice.
Figure 12B:
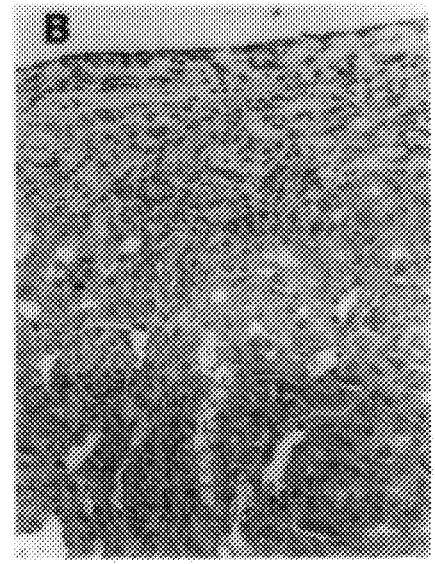

Hematoxylin and eosin staining of a control human islet grafted mouse 29 days after transplantation showed a massive lymphocyte infiltration (FIG. 12A). The same tissue, stained for insulin, showed no detectable insulin production (FIG. 12B).

Figure 12C:
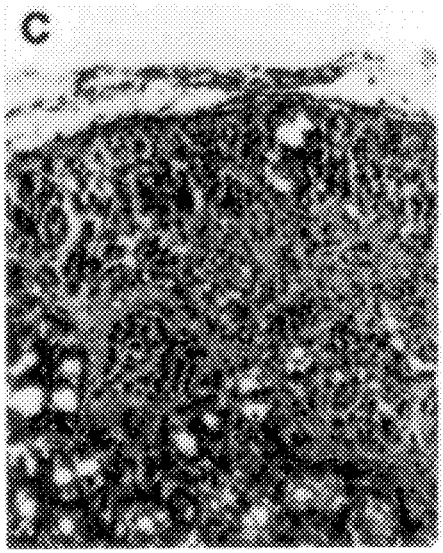
Figure 12D:
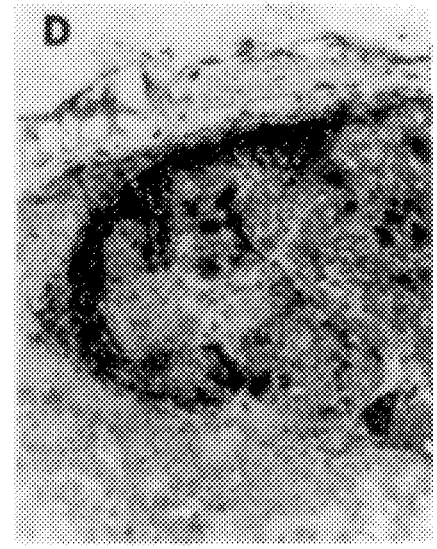

Histological examination of tissue from a CTLA4Ig-treated mouse 21 days after transplant showed intact islets under the kidney capsule with very few lymphocytes infiltrating the transplanted tissue (FIG. 12C). The tissue was stained with hematoxylin and eosin. The same tissue from the CTLA4Ig-treated mouse, stained for insulin, showed the production of insulin by the grafted islets (FIG. 12D). Similar results were observed in graft tissue examined at later time points. The upper, middle, and lower arrowheads identify the kidney capsule, islet transplant, and kidney parenchyma, respectively.

In the histopathology assay all tissues were fixed in 10% buffered formalin and processed, and 5-μm sections were stained either with hematoxylin and eosin or for insulin with the avidin-biotin-peroxidase method (S. M. Hsu, L. Raine, H. Fanger, J. Histochem, Cytochem, 29:577 (1981)). Magnification was ×122.

Figure 13:
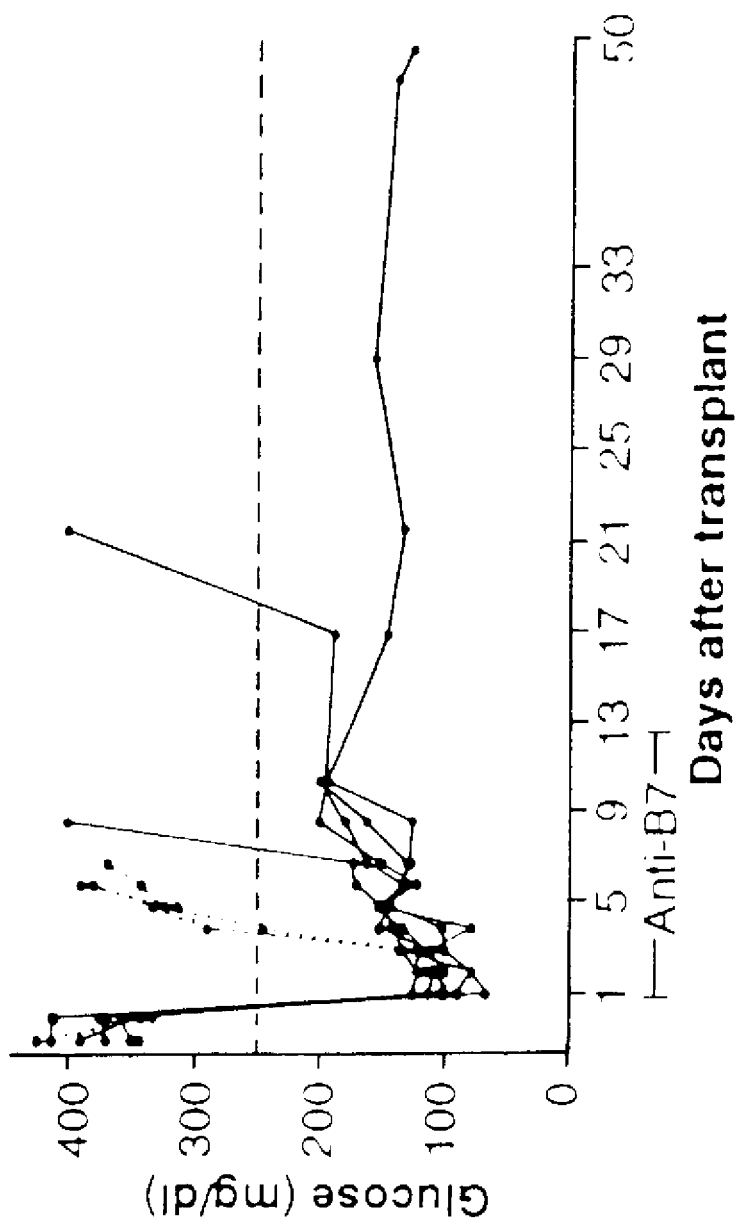
FIG. 13 is a line graph showing the prolongation of islet graft survival with MAb to human B7.

In FIG. 13 streptozotocin-treated animals were transplanted as described hereinabove for FIG. 11. The mice were treated either with PBS (dotted lines) or with MAb to human B7 (solid lines) at a dose of 50 μg every other day for 14 days (FIG. 13). Control animals (treated with PBS) (n=3) had a mean graft survival of 3.5 days, whereas anti-B7-treated animals (n=5) maintained grafts from 9 to >50 days (FIG. 13).

Figure 14:
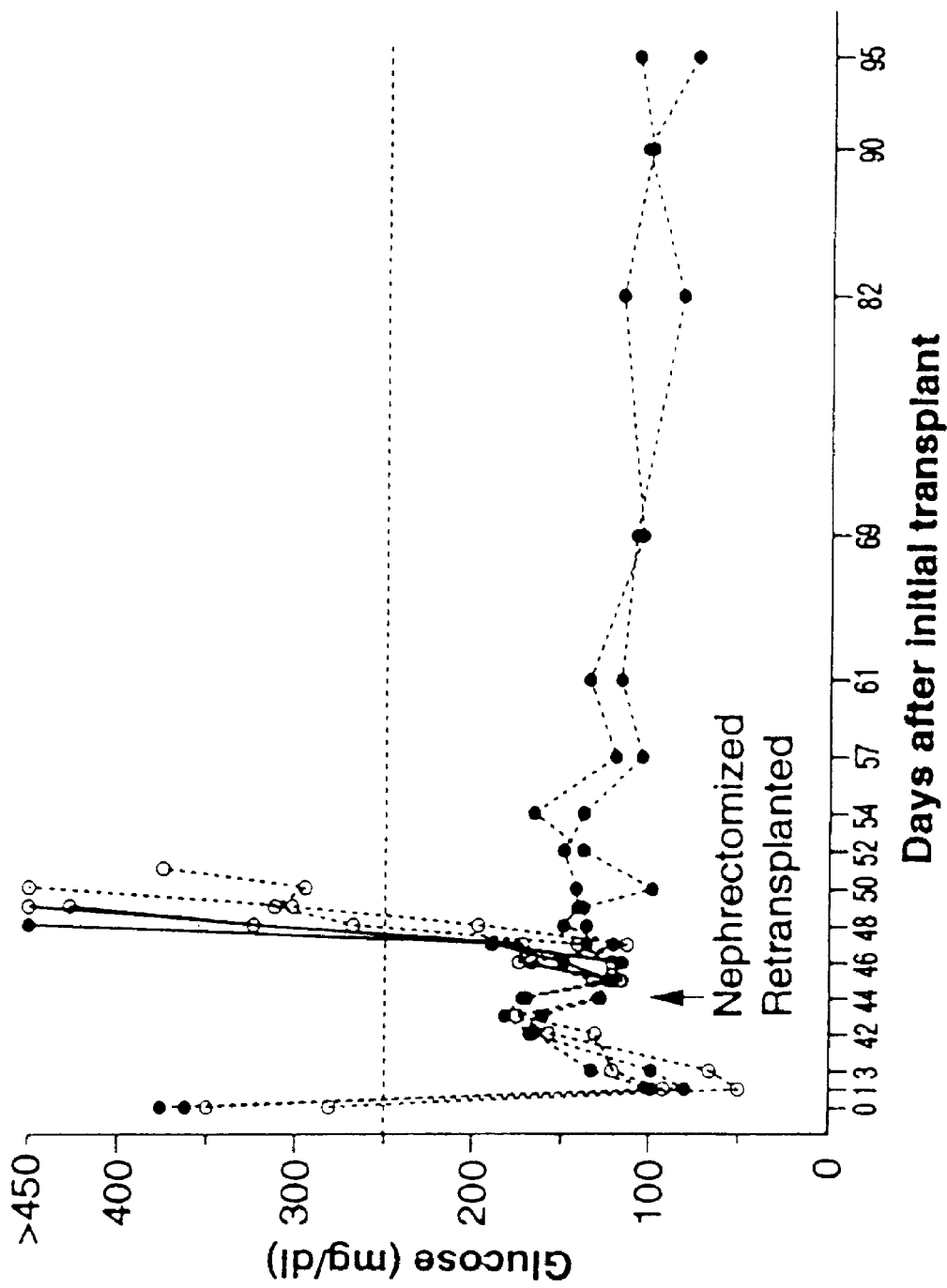
FIG. 14 is a line graph showing induction of donor-specific unresponsiveness to islet graft antigens by CTLA4Ig.

In FIG. 14 normal glycemic, CTLA4Ig-treated, transplanted mice (dotted lines) were nephrectomized on day 44 after transplant and immediately retransplanted with either 1000 first party donor islets (dotted lines, solid circles) or 1000 second party islets (dotted lines, open circles) beneath the remaining kidney capsule.

These islets, frozen at the time of the first transplant, were thawed and cultured for 3 days before transplant to ensure islet function. B10 mice that had been treated with streptozotocin and exhibited nonfasting glucose levels of greater than 280 mg/dl were used as controls (solid lines) (FIG. 14). No treatment was given after transplantation.

Control animals rejected both the first party (solid lines, closed circles) and the second party (solid lines, open circles) islet grafts by day 4 after transplant (FIG. 14). The CTLA4Ig-treated mice retransplanted with second party islets had a mean graft survival of 4.5 days, whereas animals retransplanted with first party donor islets maintained grafts for as long as analyzed (>80 days) (FIG. 14).

CTLA4Ig Significantly Prolongs Human Islet Graft Survival in Mice in a Donor-Specific Manner Thereby Providing an Approach to Immunosuppression C57BL/6 (B6) or C57BL/10 (B10) mice were treated with streptozotocin to eliminate mouse pancreatic islet B dell function. Diabetic animals were grafted under the kidney capsule, and treatment was started immediately after surgery. Survival of the islet grafts was monitored by the analysis of blood glucose concentrations.

Transplanted control animals, treated with either phosphate-buffered saline (PBS)(n=14) or L6 (a human IgG1 chimeric MAb; n=8), had a mean graft survival of 5.6 and 6.4 days, respectively (FIG. 11A).

In contrast, islet rejection was delayed in animals treated with CTLA4Ig (10 μg per day for 14 days), with four out of the seven animals exhibiting moderately prolonged mean graft survival (12.75 days), whereas the remaining three animals maintained normal glucose levels for >80 days (FIG. 11B).

This eventual increase in glucose concentration may be a result of islet exhaustion because no evidence of active cellular rejection was observed.

In the three mice that maintained long-term islet grafts, the transient increase in glucose concentrations around day 21 after the transplant may have represented a self-limited rejection episode consistent with the pharmacokinetics of CTLA4Ig clearance after therapy (P. S. Linsley et al., Science 257:792 (1992)).

In subsequent experiments, the dose of CTLA4Ig was increased to 50 μg per animal every other day for about 14 days. This treatment resulted in 100% of the animals maintaining normal islet function throughout the experiment with no signs of a rejection crisis (FIG. 11C).

In order to confirm that insulin production originated from the transplanted islets and not from the native mouse pancreas, we nephrectomized selected animals at days 21 and 29 to remove the islet grafts (FIG. 11C). In these animals, glucose concentrations increased to above 350 mg/dl within 24 hours, which indicated that the islet xenograft was responsible for maintaining normal glucose levels. It appears that the blocking of the CD28-B7 interaction inhibits xenogenic islet graft rejection.

The effects of treatment with the soluble receptor, namely CTLAIg fusion protein, were not a result of Fc binding (L6 did not effect graft rejection) or general effects on T cell or B cell function in vivo.

Historical analyses of islet xenograft from control (PBS treated) and CTLA4Ig treated mice were done (FIGS. 12A, 12B, 12C, 12D). The islet tissue from the control animal demonstrated evidence of immune rejection, with a marked lymphocytic infiltrate into the graft and few remaining islets (FIG. 12A).

Immunohistochemical staining showed that insulin-positive cells were present only rarely, and no somatostatin-positive cells were present at all (FIG. 12B). In contrast, transplant tissue from the CTLA4Ig-treated mice was devoid of any lymphocytic infiltrate (FIG. 12C).

The grafts were intact, with many islets visible. In addition, the B cells observed in the human islet tissue produced human insulin (FIG. 12D) and somatostatin.

The human CTLA4Ig used in this study reacts with both murine and human B7. One advantage of the xenogeneic transplant model is the availability of a MAb to human B7 that does not react with mouse B7 (T. Yokochi, R. D. Holly, E. A. Clark, J. Immunol. 128:823 (1982)). Thus, the role of human B7-bearing antigen-presenting cells (APCs) could be directly examined.

The mice were transplanted as described and then treated with 50 μg of MAb to human B7 every other day for 14 days after transplant. This treatment prolonged graft survival in treated mice (9 to >50 days) in comparison to that for control mice (FIG. 13). The anti-B7 MAb is unable to block rejection as effectively as CTLA4Ig.

The CTLA4Ig therapy resulted in graft acceptance in the majority of mice. However, the animals may not be tolerant. Transient immunosuppression can lead to permanent islet graft acceptance because of graft adaptation (the loss of immunogenicity as a result of the loss of APC function) (L. Hao, Y. Wang, R. G. Gill, K. J. Lafferty, J. Immunol. 139:4022 (1987); K. J. Lafferty, S. J. Prowse, M. Simeonovic, Annu. Rev. Immunol. 1:143 (1983)).

In order to differentiate between these possibilities, we nephrectomized selected xenografted, CTLA4Ig-treated mice (day 40) and retransplanted them under the remaining kidney capsule with either the original donor islets (first party) or unrelated second party human islets (FIG. 14).

Streptozotocin-treated control animals, having never received an islet graft, were also transplanted with either first or second party islets. No treatment after the transplant was given. Control animals rejected the first and second party islets by day 4. The CTLA4Ig-treated animals that had received the second party islets rejected these islets by day 5, whereas animals receiving first party donor islets maintained the grafts for >80 days (FIG. 14).

These results suggest that the CTLA4Ig treatment resulted in prolonged donor-specific unresponsiveness to the xenogeneic islets. The ability of the murine immune response to distinguish differences among the human islet donors also supports the direct recognition of the polymorphic MHC products expressed on the human islet cells.

EXAMPLE 6

Female BALB/c (H-$2^d$) and C57BL/6 (H-$2^d$)mice, 6 to 8 wk. of age were obtained from The Jackson Laboratory (Bar Harbor, Me.).

Monoclonal antibody 11B11 is a rat IgG1 anti-murine IL-4 (Ohara, J., and W. E. Paul, 1985, Production of a monoclonal antibody to and molecular characterization of B-cell stimulatory factor-1. Nature 315:333) (Verax (Lebanon, N.H.)).

BALB/c mice (five per group) were immunized intravenously with $10^8$ SRBC alone or together with 200 μg chimeric L6 mAb or human CTLA4Ig fusion protein. The indicated groups were treated 2 hrs. prior to injection of SRBCs by intraperitoneal injection of 2 mls of either rat immunoglobulin or rat anti-murine IL-4 mAb 11B11 at 5 mg/ml. Treatment with chimeric L6 mAb or CTLA4Ig was repeated daily for 4 additional days.

All animals were given intravenous injections of SRBCs (FIG. 15) or KLH (FIG. 16) on day 46. Specifically, in FIG. 15, the closed box represents mice who were administered with only SRBC at day 0 and day 46. The open box represents mice administered with only SRBC at day 46. The remaining mice represented in FIG. 15 were further administered with SRBC at day 46. In contrast, in FIG. 16, the mice were administered with a different immunogen, KLH, at day 46 only.

Serum concentrations of mice measured as having antibodies directed against SRBCs or KLH were determined by ELISA as described (Linsley et al., Science 1992).

Serum antibody titers were calculated as the dilution giving an $A_{450}$ of five times background. Serum antibody titer values from FIG. 15 were determined from pooled sera from five mice per group, while serum antibody titer values from FIG. 16 represents mean titers of five individual sera. Arrows indicate an SRBC or KLH injection at day 46.

Figure 15:
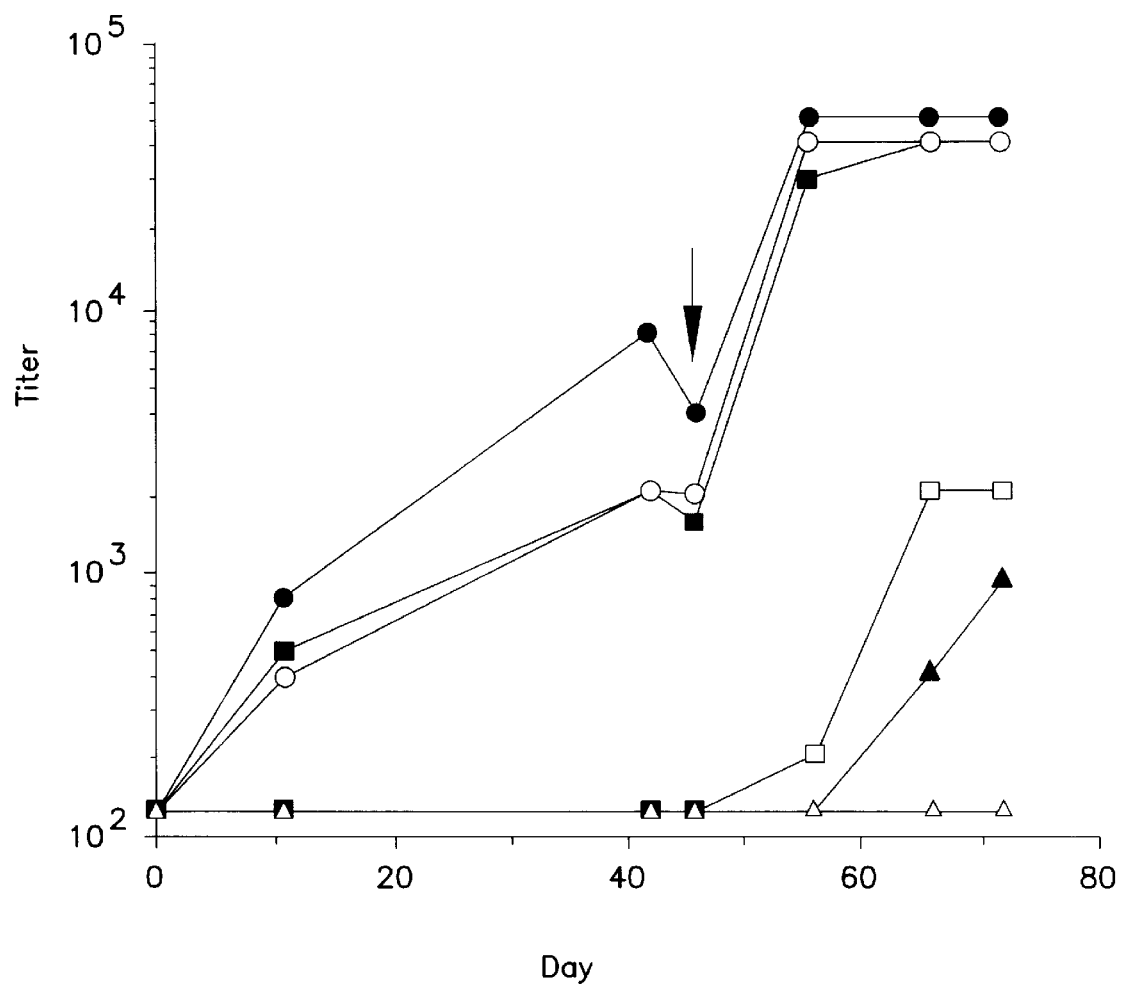
FIG. 15 is a line graph showing antibody serum titer levels of mice injected with sheep red blood cells (SRBC), mAb L6 and rat Ig, mAb L6 and anti-IL4, CTLA4Ig and rat Ig, CTLA4Ig and anti-IL4. The X axis measures the antibody-serum titer. The Y axis measures time in days. The closed box represents mice injected with SRBC at day 0 and day 46. The open box represents mice injected with SRBC at day 46. The closed circle represents mice injected with mAb L6 and rat immunoglobulin. The open circle represents mice injected with mAb L6 and anti-IL4 antibody. The closed triangle represents mice injected with CTLA4Ig and rat immunoglobulin. The open triangle represents mice injected with CTLA4Ig and anti-IL4 antibody.
Figure 16:
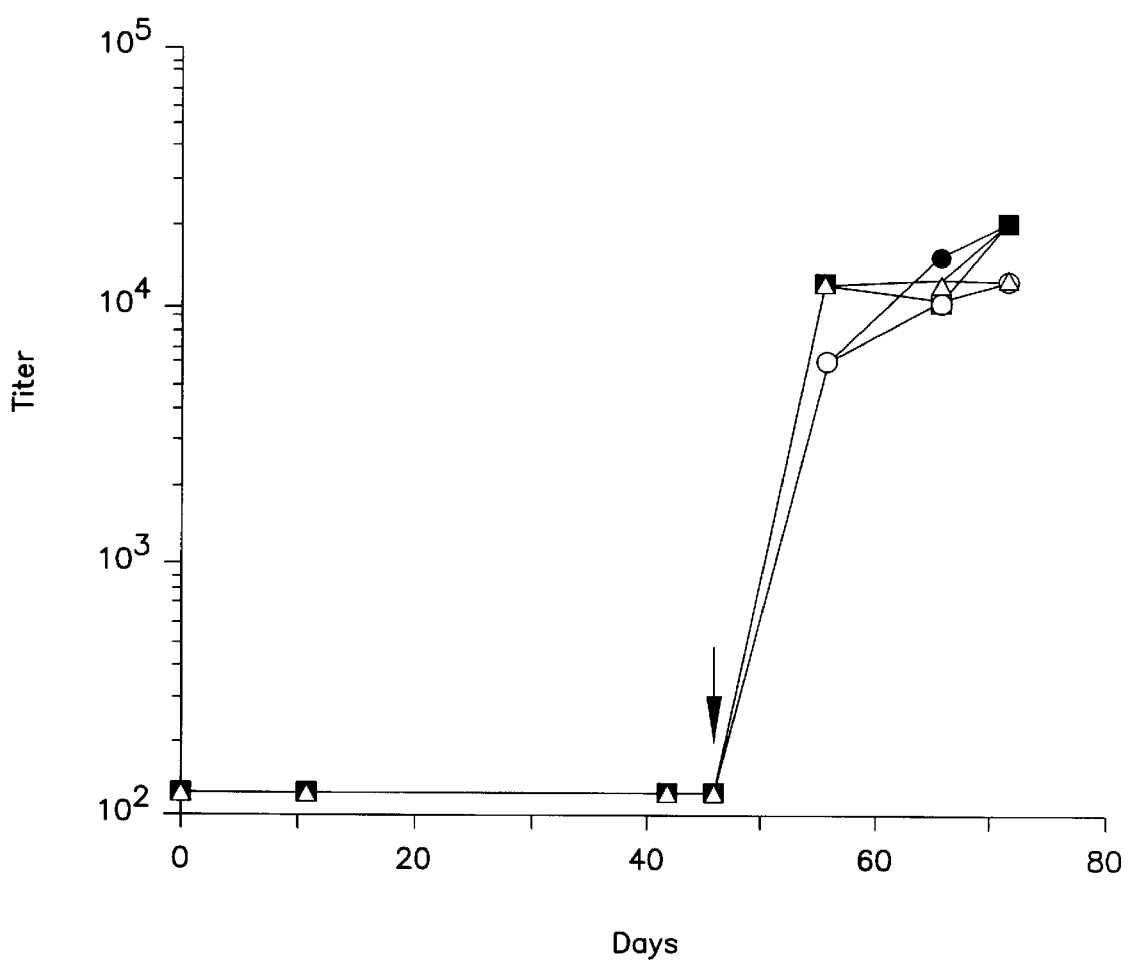
FIG. 16 is a line graph showing antibody serum titer levels of mice injected with KLH, mAb L6 and rat Ig, mAb L6 and anti-IL4, CTLA4Ig and rat Ig, CTLA4Ig and anti-IL4. The X axis measures the antibody-serum titer. The Y axis measures time in days. The closed box represents mice injected with keyhole limpet hemocyanin (KLH) at day 46. The closed circle represents mice injected with mAb L6 and rat immunoglobulin. The open circle represents mice injected with mAb L6 and anti-IL4 antibody. The closed triangle represents mice injected with CTLA4Ig and rat immunoglobulin. The open triangle represents mice injected with CTLA4Ig and anti-IL4 antibody.

FIGS. 15 and 16 show that the immunological response in mice injected concurrently with both CTLA4Ig and anti-IL4 (open triangle) is suppressed in an antigen-specific manner.

FIG. 15 shows that there is no rise in serum antibody titer (i.e. no primary or secondary immunological response) in mice injected concurrently with CTLA4Ig and anti-IL4 and injected with SRBC at day 0 and day 46. The combination of CTLA4Ig and anti-IL4 suppresses a primary and secondary immune response and induces long lasting immunological non-responsiveness to SRBC.

Additionally, FIG. 15 shows that there is no primary immunological response in mice injected concurrently with CTLA4Ig and the control rat Ig (Cappel, Organontecknika, Palo Alto, Calif.). However, these mice exhibit a secondary immunological response after injection with SRBC at day 46 (closed triangle, FIG. 15).

FIG. 16 shows that administration of CTLA4Ig and anti-IL4, followed by a different immunogen, KLH, at day 46 in mice does not suppress a primary immune response to KLH in mice. Instead, these mice exhibited a primary immune response to KLH (open triangle, FIG. 16). Thus, mice treated with CTLA4Ig and anti-IL4 exhibited a highly specific immune response depending on the antigen administered therein.

What is claimed is:

1. A method for suppressing an immune response comprising contacting B7-positive lymphocytes with a B7-binding molecule and an IL4-binding molecule, wherein an immune response is thereby suppressed.

2. The method of claim 1, wherein the immune response is a B cell response.

3. The method of claim 1, wherein the immune response is a T cell response.

4. A method for inhibiting tissue transplant rejection by a subject, the subject being a recipient of transplanted tissue, which method comprises administering to the subject a B7-binding molecule and an IL4-binding molecule so a primary and secondary immune response is suppressed thereby inhibiting tissue transplant rejection by the subject.

5. A method for inhibiting graft versus host disease in a subject which method comprises administering to the subject a B7-binding molecule and an IL4-binding molecule so a primary and secondary immune response is suppressed thereby inhibiting tissue transplant rejection by the subject.

6. The method of claim 1, 4, or 5, wherein the B7-binding molecule is a CTLA4Ig fusion protein.

7. The method of claim 6, wherein the CTLA4Ig fusion protein is a fusion protein having a first amino acid sequence containing amino acid residues from position 1 to position 125 of the amino acid sequence corresponding to the extracellular domain of CTLA4 and a second amino acid sequence containing amino acid residues corresponding to the hinge, CH2 and CH3 regions of human immunoglobulin Cγ1.

8. The method of claim 1, 4, or 5, wherein the B7-binding molecule is a CD28Ig/CTLA4Ig fusion protein hybrid.

9. The method of claim 8, wherein the CD28Ig/CTLA4Ig fusion protein hybrid is a fusion protein hybrid having a first amino acid sequence consisting of a portion of the extracellular domain of CD28 receptor which portion binds B7 fused to a second amino acid sequence consisting of a portion of the extracellular domain of CTLA4 receptor which portion binds B7 and a third amino acid sequence of the hinge, CH2 and CH3 regions of human immunoglobulin Cγ1.

10. The method of claim 1, 4, or 5, wherein the IL4-binding molecule is a monoclonal antibody which specifically recognizes and binds to IL4.

11. The method of claim 1, 4, or 5, wherein the IL4-binding molecule is a soluble IL4 receptor which recognizes and binds to IL4.

\* \* \* \* \*

UNITED STATES PATENT AND TRADEMARK OFFICE
CERTIFICATE OF CORRECTION

PATENT NO. : 5,770,197
DATED : June 23, 1998
INVENTOR(S) : Linsley et al.

It is certified that error appears in the above-identified patent and that said Letters Patent is hereby corrected as shown below:

Title page,
Item [63], Related U.S. Application Data, "Jul." should read -- Jun. --

Column 1,
Line 7, "Jul." should read -- Jun. --

Signed and Sealed this

Eighth Day of March, 2005

JON W. DUDAS
*Director of the United States Patent and Trademark Office*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:1:

CTAGCCACTG  AAGCTTCACC  ATGGGTGTAC  TGCTCACAC 39

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:2:

TGGCATGGGC  TCCTGATCAG  GCTTAGAAGG  TCCGGGAAA 39

( 2 ) INFORMATION FOR SEQ ID NO:3:

( i ) SEQUENCE CHARACTERISTICS:
        ( A ) LENGTH: 39 base pairs
        ( B ) TYPE: nucleic acid (C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:3:

```
TTTGGGCTCC  TGATCAGGAA  AATGCTCTTG  CTTGGTTGT                              39
```

(2) INFORMATION FOR SEQ ID NO:4:

(i) SEQUENCE CHARACTERISTICS:
    (A) LENGTH: 84 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:4:

```
AAGCAAGAGC  ATTTTCCTGA  TCAGGAGCCC  AAATCTTCTG  ACAAAACTCA  CACATCCCCA    60
CCGTCCCCAG  CACCTGAACT  CCTG                                              84
```

(2) INFORMATION FOR SEQ ID NO:5:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:5:

```
CTTCGACCAG  TCTAGAAGCA  TCCTCGTGCG  ACCGCGAGAG  C                         41
```

(2) INFORMATION FOR SEQ ID NO:6:

(i) SEQUENCE CHARACTERISTICS:
    (A) LENGTH: 47 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens ( x i ) SEQUENCE DESCRIPTION: SEQ ID NO:6:

CATTGCACAG TCAAGCTTCC ATGCCCATGG GTTCTCTGGC CACCTTG 47

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:7:

ATCCACAGTG CAGTGATCAT TTGGATCCTG GCATGTGAC 39

( 2 ) INFORMATION FOR SEQ ID NO:8:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:8:

CTCAGTCTGG TCCTTGCACT CCTGTTTCCA AGCATGGCGA GCATGGCAAT GCACGTGGCC 60

CAGCC 65

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:9:

TTTGGGCTCC TGATCAGAAT CTGGGCACGG TTG 33

( 2 ) INFORMATION FOR SEQ ID NO:10:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:10:

```
CTAGCCACTG AAGCTTCACC AATGGGTGTA CTGCTCACAC AGAGGACGCT GCTCAGTCTG    60

GTCCTTGCAC TC                                                       72
```

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:11:

```
GCAATGCACG TGGCCCAGCC TGCTGTGGTA GTG                                 33
```

( 2 ) INFORMATION FOR SEQ ID NO:12:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:12:

```
TGATGTAACA TGTCTAGATC AATTGATGGG AATAAAATAA GGCTG                    45
```

( 2 ) INFORMATION FOR SEQ ID NO:13:

( i ) SEQUENCE CHARACTERISTICS:
        ( A ) LENGTH: 561 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS (B) LOCATION: 1..561

(xi) SEQUENCE DESCRIPTION: SEQ ID NO:13:

| | | | | | | | | | | | | | | | | |
|---|---|---|---|---|---|---|---|---|---|---|---|---|---|---|---|---|
| GCA | ATG | CAC | GTG | GCC | CAG | CCT | GCT | GTG | GTA | CTG | GCC | AGC | AGC | CGA | GGC | 48 |
| Ala | Met | His | Val | Ala | Gln | Pro | Ala | Val | Val | Leu | Ala | Ser | Ser | Arg | Gly | |
| 1 | | | | 5 | | | | | 10 | | | | | 15 | | |
| ATC | GCC | AGC | TTT | GTG | TGT | GAG | TAT | GCA | TCT | CCA | GGC | AAA | GCC | ACT | GAG | 96 |
| Ile | Ala | Ser | Phe | Val | Cys | Glu | Tyr | Ala | Ser | Pro | Gly | Lys | Ala | Thr | Glu | |
| | | | 20 | | | | | 25 | | | | | 30 | | | |
| GTC | CGG | GTG | ACA | GTG | CTT | CGG | CAG | GCT | GAC | AGC | CAG | GTG | ACT | GAA | GTC | 144 |
| Val | Arg | Val | Thr | Val | Leu | Arg | Gln | Ala | Asp | Ser | Gln | Val | Thr | Glu | Val | |
| | | 35 | | | | | 40 | | | | | 45 | | | | |
| TGT | GCG | GCA | ACC | TAC | ATG | ATG | GGG | AAT | GAG | TTG | ACC | TTC | CTA | GAT | GAT | 192 |
| Cys | Ala | Ala | Thr | Tyr | Met | Met | Gly | Asn | Glu | Leu | Thr | Phe | Leu | Asp | Asp | |
| | 50 | | | | | 55 | | | | | 60 | | | | | |
| TCC | ATC | TGC | ACG | GGC | ACC | TCC | AGT | GGA | AAT | CAA | GTG | AAC | CTC | ACT | ATC | 240 |
| Ser | Ile | Cys | Thr | Gly | Thr | Ser | Ser | Gly | Asn | Gln | Val | Asn | Leu | Thr | Ile | |
| 65 | | | | | 70 | | | | | 75 | | | | | 80 | |
| CAA | GGA | CTG | AGG | GCC | ATG | GAC | ACG | GGA | CTC | TAC | ATC | TGC | AAG | GTG | GAG | 288 |
| Gln | Gly | Leu | Arg | Ala | Met | Asp | Thr | Gly | Leu | Tyr | Ile | Cys | Lys | Val | Glu | |
| | | | | 85 | | | | | 90 | | | | | 95 | | |
| CTC | ATG | TAC | CCA | CCG | CCA | TAC | TAC | CTG | GGC | ATA | GGC | AAC | GGA | ACC | CAG | 336 |
| Leu | Met | Tyr | Pro | Pro | Pro | Tyr | Tyr | Leu | Gly | Ile | Gly | Asn | Gly | Thr | Gln | |
| | | | 100 | | | | | 105 | | | | | 110 | | | |
| ATT | TAT | GTA | ATT | GAT | CCA | GAA | CCG | TGC | CCA | GAT | TCT | GAC | TTC | CTC | CTC | 384 |
| Ile | Tyr | Val | Ile | Asp | Pro | Glu | Pro | Cys | Pro | Asp | Ser | Asp | Phe | Leu | Leu | |
| | | 115 | | | | | 120 | | | | | 125 | | | | |
| TGG | ATC | CTT | GCA | GCA | GTT | AGT | TCG | GGG | TTG | TTT | TTT | TAT | AGC | TTT | CTC | 432 |
| Trp | Ile | Leu | Ala | Ala | Val | Ser | Ser | Gly | Leu | Phe | Phe | Tyr | Ser | Phe | Leu | |
| | 130 | | | | | 135 | | | | | 140 | | | | | |
| CTC | ACA | GCT | GTT | TCT | TTG | AGC | AAA | ATG | CTA | AAG | AAA | AGA | AGC | CCT | CTT | 480 |
| Leu | Thr | Ala | Val | Ser | Leu | Ser | Lys | Met | Leu | Lys | Lys | Arg | Ser | Pro | Leu | |
| 145 | | | | | 150 | | | | | 155 | | | | | 160 | |
| ACA | ACA | GGG | GTC | TAT | GTG | AAA | ATG | CCC | CCA | ACA | GAG | CCA | GAA | TGT | GAA | 528 |
| Thr | Thr | Gly | Val | Tyr | Val | Lys | Met | Pro | Pro | Thr | Glu | Pro | Glu | Cys | Glu | |
| | | | | 165 | | | | | 170 | | | | | 175 | | |
| AAG | CAA | TTT | CAG | CCT | TAT | TTT | ATT | CCC | ATC | AAT | | | | | | 561 |
| Lys | Gln | Phe | Gln | Pro | Tyr | Phe | Ile | Pro | Ile | Asn | | | | | | |
| | | | 180 | | | | | 185 | | | | | | | | |

(2) INFORMATION FOR SEQ ID NO:14:

(i) SEQUENCE CHARACTERISTICS:
        (A) LENGTH: 187 amino acids
        (B) TYPE: amino acid
        (D) TOPOLOGY: linear (ii) MOLECULE TYPE: protein (xi) SEQUENCE DESCRIPTION: SEQ ID NO:14:

| | | | | | | | | | | | | | | | |
|---|---|---|---|---|---|---|---|---|---|---|---|---|---|---|---|
| Ala | Met | His | Val | Ala | Gln | Pro | Ala | Val | Val | Leu | Ala | Ser | Ser | Arg | Gly |
| 1 | | | | 5 | | | | | 10 | | | | | 15 | |
| Ile | Ala | Ser | Phe | Val | Cys | Glu | Tyr | Ala | Ser | Pro | Gly | Lys | Ala | Thr | Glu |
| | | | 20 | | | | | 25 | | | | | 30 | | |
| Val | Arg | Val | Thr | Val | Leu | Arg | Gln | Ala | Asp | Ser | Gln | Val | Thr | Glu | Val |
| | | 35 | | | | | 40 | | | | | 45 | | | |
| Cys | Ala | Ala | Thr | Tyr | Met | Met | Gly | Asn | Glu | Leu | Thr | Phe | Leu | Asp | Asp |
| | 50 | | | | | 55 | | | | | 60 | | | | |
| Ser | Ile | Cys | Thr | Gly | Thr | Ser | Ser | Gly | Asn | Gln | Val | Asn | Leu | Thr | Ile |
| 65 | | | | | 70 | | | | | 75 | | | | | 80 |
| Gln | Gly | Leu | Arg | Ala | Met | Asp | Thr | Gly | Leu | Tyr | Ile | Cys | Lys | Val | Glu |

|  | 85 |  |  |  |  | 90 |  |  |  |  | 95 |  |  |
|---|---|---|---|---|---|---|---|---|---|---|---|---|---|
| Leu | Met | Tyr | Pro 100 | Pro | Pro | Tyr | Tyr | Leu 105 | Gly | Ile | Gly | Asn | Gly 110 | Thr | Gln |
| Ile | Tyr | Val 115 | Ile | Asp | Pro | Glu | Pro 120 | Cys | Pro | Asp | Ser | Asp 125 | Phe | Leu | Leu |
| Trp | Ile 130 | Leu | Ala | Ala | Val | Ser 135 | Ser | Gly | Leu | Phe | Phe 140 | Tyr | Ser | Phe | Leu |
| Leu 145 | Thr | Ala | Val | Ser | Leu 150 | Ser | Lys | Met | Leu | Lys 155 | Lys | Arg | Ser | Pro | Leu 160 |
| Thr | Thr | Gly | Val | Tyr 165 | Val | Lys | Met | Pro | Pro 170 | Thr | Glu | Pro | Glu | Cys 175 | Glu |
| Lys | Gln | Phe | Gln 180 | Pro | Tyr | Phe | Ile | Pro 185 | Ile | Asn |  |  |  |  |  |